(12) United States Patent
Cruse et al.

(10) Patent No.: US 7,074,876 B2
(45) Date of Patent: *Jul. 11, 2006

(54) BLOCKED MERCAPTOSILANE COUPLING AGENTS FOR FILLED RUBBERS

(75) Inventors: Richard W. Cruse, Yorktown Heights, NY (US); Robert J. Pickwell, Tonawanda, NY (US); Keith J. Weller, Yonkers, NY (US); Eric R. Pohl, Mt. Kisco, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/986,515

(22) Filed: Nov. 9, 2001

(65) Prior Publication Data

US 2002/0055564 A1 May 9, 2002

Related U.S. Application Data

(62) Division of application No. 09/284,841, filed as application No. PCT/US98/17391 on Aug. 21, 1998, now Pat. No. 6,414,061.

(60) Provisional application No. 60/056,566, filed on Aug. 21, 1997.

(51) Int. Cl.
C07F 7/04 (2006.01)
C07F 7/08 (2006.01)
C07F 7/10 (2006.01)
C07F 9/165 (2006.01)
C07F 9/38 (2006.01)

(52) U.S. Cl. .......................... 528/44; 528/61; 528/250; 528/251; 560/307; 560/308; 560/310

(58) Field of Classification Search ................ 524/262, 524/392, 265, 267, 282, 283; 558/251, 250, 558/44, 61; 560/307, 308, 310; 528/44, 528/61, 250, 251
See application file for complete search history.

(56) References Cited

U.S. PATENT DOCUMENTS

| | | | |
|---|---|---|---|
| 3,502,704 A | 3/1970 | McKeller | 260/448.8 |
| 3,692,812 A | 9/1972 | Berger | 260/448.2 |
| 3,922,436 A | 11/1975 | Bell et al. | 428/375 |
| 3,957,718 A | 5/1976 | Pochert et al. | 260/38 |
| 4,060,539 A | 11/1977 | Seiler et al. | 260/448.8 |

(Continued)

FOREIGN PATENT DOCUMENTS

AU 10082/97 7/1997

(Continued)

OTHER PUBLICATIONS

Gornowica, G. A., et al; "Preparation of Silylalkanethiols"; The Journal of Organic ChemistryI; vol. 33; No. 7; Jul. 1968; pp. 2918-2924.

(Continued)

Primary Examiner—Kelechi C. Egwim
(74) Attorney, Agent, or Firm—Dominick G. Vicari

(57) ABSTRACT

Disclosed herein is a blocked mercaptosilane selected from the group consisting of $$[[(ROC(=O))_p-(G)_j]_k-Y-S]_r-G-(SiX_3)_s; \text{ and} \quad (1)$$

$$[(X_3Si)_q-G]_a-[Y-[S-G-SiX_3]_b]_c \quad (2)$$

wherein

Y is a polyvalent species $(Q)_zA(=E)$ selected from the group consisting of —C(=NR)—; —SC(=NR)—; —SC(=O)—; —OC(=O)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(—)$_2$; (—S)$_2$P(=S)—; —(—S)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—; wherein the atom A attached to unsaturated heteroatom E is attached to the sulfur which in turn is linked via a group G to the silicon atom;

each R is chosen independently from hydrogen, straight, cyclic, or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl, or aralkyl, wherein G can contain from 1 to 18 carbon atoms, with the proviso that G is not such that the blocked mercaptosilane would contain an α,β-unsaturated carbonyl that can undergo polymerization reactions, and if G is univalent, G can be a hydrogen atom;

X is independently selected from the group consisting of —Cl, —Br, RO—, RC(=O)O—, R$_2$C=NO—, R$_2$NO—, R$_2$N—, —R, and —(OSiR$_2$)$_t$(OSiR$_3$) wherein each R is as above and at least one X is not —R;

p is 0 to 5; r is 1 to 3; z is 0 to 2; q is 0 to 6; a is 0 to 7; b is 1 to 3; j is 0 to 1, but it may be 0 only if p is 1; c is 1 to 6; t is 0 to 5; s is 1 to 3; k is 1 to 2; with the provisos that (I) if A is carbon, sulfur or sulfonyl, then (i) a+b is 2 and (ii) k is 1; (II) if A is phosphorus, then a+b is 3 unless both (i) c is greater than 1 and (ii) b is 1, in which case a is c+1; and (III) if A is phosphorus, then k is 2.

11 Claims, No Drawings

U.S. PATENT DOCUMENTS

| | | | |
|---|---|---|---|
| 4,152,347 A * | 5/1979 | Pletka et al. | 556/405 |
| 4,184,998 A | 1/1980 | Shippy et al. | 260/42.15 |
| 4,519,430 A | 5/1985 | Ahmad et al. | 152/209 |
| 4,820,751 A | 4/1989 | Takeshita et al. | 523/215 |
| 5,070,215 A * | 12/1991 | Bambury et al. | 556/418 |
| 5,116,886 A | 5/1992 | Wolff et al. | 523/209 |
| 5,770,754 A | 6/1998 | Scholl | 556/427 |
| 6,127,468 A * | 10/2000 | Cruse et al. | 524/225 |
| 6,140,393 A | 10/2000 | Bomal et al. | 523/213 |
| 6,204,339 B1 * | 3/2001 | Waldman et al. | 525/350 |
| 6,274,753 B1 | 8/2001 | Krafczyk et al. | 556/405 |
| 6,303,821 B1 | 10/2001 | Wideman et al. | 564/328 |
| 6,608,125 B1 | 8/2003 | Cruse et al. | |
| 6,635,700 B1 | 10/2003 | Cruse et al. | |
| 6,649,684 B1 | 11/2003 | Okel | |
| 6,777,569 B1 | 8/2004 | Westmeyer et al. | |
| 2002/0055564 A1 | 5/2002 | Cruse et al. | |
| 2002/0055568 A1 | 5/2002 | Cruse et al. | |
| 2002/0055646 A1 | 5/2002 | Cruse et al. | |
| 2002/0099118 A1 | 7/2002 | Cruse et al. | |
| 2002/0115767 A1 | 8/2002 | Cruse et al. | |
| 2003/0199619 A1 | 10/2003 | Cruse | |
| 2003/0225195 A1 | 12/2003 | Cruse et al. | |
| 2004/0021133 A1 | 2/2004 | Nagpal et al. | |
| 2004/0198881 A1 | 10/2004 | Cruse et al. | |
| 2004/0210001 A1 | 10/2004 | Cruse et al. | |

FOREIGN PATENT DOCUMENTS

| | | |
|---|---|---|
| DE | 2508931 | 9/1976 |
| EP | 631982 | 1/1985 |
| JP | 63270751 | 11/1988 |
| WO | 98/17391 | 4/1998 |

OTHER PUBLICATIONS van Turnhout, C. M., Ed.; Rubber Chemicals; Plastics & Rubber Research Institute TNO, Delft—Holland; D. Reidel Publishing Company, Inc., Boston, Massachusetts; ISBN 90 277 0349 3, 1973.

Meeting Minutes, Improved Performance of Silica and Carbon Black Filled Elastomers, Dec. 1998. (Copy Provided in Parent Application).

Trialkoxysilylalkanethiols and Bis (trialkoxysilylakly) sulfides—XP-002084434, Aug. 1977. (Copy Provided in Parent Application).

Epoxy Resins Potting Compositions for Semiconductor Devices XP-002084435—Sep. 1989. (Copy Provided in Parent Application).

Vanderbilt Rubber Handbook (1978), pp. 344-346.

Gornowicz et al., Preparation of Silylalkanethiols, The Journal of Organic Chemistry, vol. 33, No. 7, pp. 2918-2924, Jul. 1968.

* cited by examiner

BLOCKED MERCAPTOSILANE COUPLING AGENTS FOR FILLED RUBBERS

CROSS REFERENCE TO RELATED APPLICATION

This is a division of application Ser. No. 09/284,841, filed Apr. 1, 1999, U.S. Pat. No. 6,414,061 which is a 371 of PCT/US98/17391, Aug. 21, 1998, which claims priority to U.S. Provisional Patent Application No. 60/056,566, filed Aug. 21, 1997.

FIELD OF THE INVENTION

This invention relates to sulfur silane coupling agents which are latent, that is, they are in a state of reduced activity until such a time as one finds it useful to activate them. The invention also relates to the manufacture of rubbers including inorganic fillers and these silane coupling agents, as well as to the manufacture of the silanes.

BACKGROUND

The majority of art in the use of sulfur-containing coupling agents in rubber involves silanes containing one or more of the following chemical bond types:

S—H (mercapto), S—S (disulfide or polysulfide), or C=S (thiocarbonyl). Mercaptosilanes have offered superior coupling at substantially reduced loadings; however, their high chemical reactivity with organic polymers leads to unacceptably high viscosities during processing and premature curing (scorch). Their undesirability is aggravated by their odor. As a result, other, less reactive coupling agents have been found. Hence, a compromise must be found between coupling and the associated final properties, processability, and required loading levels, which invariably leads to the need to use substantially higher coupling agent loadings than would be required with mercaptosilanes, and often also to the need to deal with less than optimal processing conditions, both of which lead to higher costs.

The prior art discloses acylthioalkyl silanes, such as $CH_3C(=O)S(CH_2)_{1-3}Si(OR)_3$ (M. G. Voronkov et al. in *Inst. Org. Khim.*, Irkutsk, Russia) and $HOC(=O)CH_2CH_2C(=O)S(CH_2)_3Si(OC_2H_5)_3$ (U.S. Pat. No. 3,922,436 to R. Bell et al.). Takeshita and Sugawara disclosed in Japanese Patent JP 63270751 A2 the use of compounds represented by the general formula $CH_2=C(CH_3)C(=O)S(CH_2)_{1-6}Si(OCH_3)_3$ in tire tread compositions; but these compounds are not desirable because the unsaturation α,β to the carbonyl group of the thioester has the undesirable potential to polymerize during the compounding process or during storage.

Prior art by Yves Bomal and Olivier Durel in Australian Patent AU-A-10082/97 discloses the use in rubber of silanes of the structure represented by $R^1{}_nX_{3-n}Si—(Alk)_m(Ar)_p—S(C=O)—R$ where $R^1$ is phenyl or alkyl; X is halogen, alkoxy, cycloalkoxy, acyloxy, or OH; Alk is alkyl; Ar is aryl; R is alkyl, alkenyl, or aryl; n is 0 to 2; and m and p are each 0 or 1, but not both zero. This prior art, however, stipulates that compositions of the structures of Formula (1P) must be used in conjunction with functionalized siloxanes. In addition, the prior art does not disclose or suggest the use of compounds of Formula (1P) as latent mercaptosilane coupling agents, nor does it disclose or suggest the use of these compounds in any way which would give rise to the advantages of using them as a source of latent mercaptosilane.

U.S. Pat. Nos. 4,519,430 to Ahmad et al. and 4,184,998 to Shippy et al. disclose the blocking of a mercaptosilane with an isocyanate to form a solid which is added to a tire composition, which mercaptan reacts into the tire during heating, which could happen at any time during processing since this is a thermal mechanism. The purpose of this silane is to avoid the sulfur smell of the mercaptosilane, not to improve the processing of the tire. Moreover, the isocyanate used has toxicity issues when used to make the silane and when released during rubber processing.

U.S. Pat. No. 3,957,718 to Porchet et al. discloses compositions containing silica, phenoplasts or aminoplasts, and silanes, such as xanthates, thioxanthates, and dithiocarbamates; however, the prior art does not disclose or suggest the use of these silanes as latent mercaptosilane coupling agents, nor does it suggest or disclose the advantage of using them as a source of latent mercaptosilane. There remains a need for effective latent coupling agents which exhibit the advantages of mercaptosilanes without exhibiting the disadvantages such as described herein.

SUMMARY OF THE INVENTION

The silanes of the present invention are mercaptosilane derivatives in which the mercapto group is blocked ("blocked mercaptosilanes"), i.e., the mercapto hydrogen atom is replaced by another group (hereafter referred to as "blocking group"). Specifically, the silanes of the present invention are blocked mercaptosilanes in which the blocking group contains an unsaturated heteroatom or carbon chemically bound directly to sulfur via a single bond. This blocking group optionally may be substituted with one or more carboxylate ester or carboxylic acid functional groups. The use of these silanes in the manufacture of inorganic filled rubbers is taught wherein they are deblocked by the use of a deblocking agent during the manufacturing process. The manufacture of such silanes is taught as well.

DETAILED DESCRIPTION OF THE INVENTION

Silane Structures

The blocked mercaptosilanes can be represented by the Formulae (1-2):

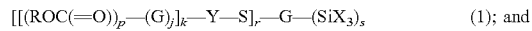

(1); and

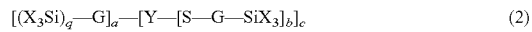

(2)

wherein

Y is a polyvalent species $(Q)_zA(=E)$, preferably selected from the group consisting of —C(=NR)—; —SC(=NR)—; —SC(=O)—; (—NR)C(=O)—; (—NR)C(=S)—; —OC(=O)—; —OC(=S)—; —C(=O)—; —SC(=S)—; —C(=S)—; —S(=O)—; —S(=O)$_2$—; —OS(=O)$_2$—; (—)S(=O)$_2$—; —SS(=O)—; —OS(=O)—; (—NR)S(=O)—; —SS(=O)$_2$—; (—S)$_2$P(=O)—; —(—S)P(=O)—; —P(=O)(—)$_2$; (—S)$_2$P(=S)—; —(—)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—; each wherein the atom (A) attached to the unsaturated heteroatom (E) is attached to the sulfur, which in turn is linked via a group G to the silicon atom;

each R is chosen independently from hydrogen, straight, cyclic, or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl, or aralkyl wherein G can contain from 1 to 18 carbon atoms, with the proviso that G is not such that the silane would contain an $\alpha,\beta$-unsaturated carbonyl including a carbon-carbon double bond next to the thiocarbonyl group, and if G directly bonded to Y is univalent (i.e., if p=0), G can be a hydrogen atom;

X is independently selected from the group consisting of —Cl, —Br, RO—, RC(=O)O—, $R_2$C=NO—, $R_2$NO— or $R_2$N—, —R, —(OSi$R_2$),(OSi$R_3$) wherein each R and G is as above and at least one X is not —R;

Q is oxygen, sulfur, or (—NR—);

A is carbon, sulfur, phosphorus, or sulfonyl;

E is oxygen, sulfur, or NR;

p is 0 to 5; r is 1 to 3; z is 0 to 2; p is 0 to 6; a is 0 to 7; b is 1 to 3; j is 0 to 1, but it may be 0 only if p is 1; c is 1 to 6, preferably 1 to 4; t is 0 to 5; s is 1 to 3; k is 1 to 2; with the provisos that (A) if A is carbon, sulfur, or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

As used herein, "alkyl" includes straight, branched, and cyclic alkyl groups, and "alkenyl" includes straight, branched, and cyclic alkenyl groups containing one or more carbon-carbon double bonds. Specific alkyls include methyl, ethyl, propyl, isobutyl, and specific aralkyls include phenyl, tolyl, and phenethyl. As used herein, "cyclic alkyl" or "cyclic alkenyl" also includes bicyclic and higher cyclic structures, as well as cyclic structures further substituted with alkyl groups. Representative examples include norbornyl, norbornenyl, ethylnorbornyl, ethylnorbornenyl, ethylcyclohexyl, ethylcyclohexenyl, and cyclohexylcyclohexyl.

Representative examples of the functional groups (—YS—) present in the silanes of the present invention include thiocarboxylate ester, —C(=O)S— (any silane with this functional group is a "thiocarboxylate ester silane"); dithiocarboxylate, —C(=S)S— (any silane with this functional group is a "dithiocarboxylate ester silane"); thiocarbonate ester, —O—C(=O)S— (any silane with this functional group is a "thiocarbonate ester silane"); dithiocarbonate ester, —S—C(=O)S— and —O—C(=S)S— (any silane with this functional groups is a "dithiocarbonate ester silane"); trithiocarbonate ester, —S—C(=S)S— (any silane with this functional group is a "trithiocarbonate ester silane"); dithiocarbamate ester, (—N—)C(=S)S— (any silane with this functional group is a "dithiocarbamate ester silane"); thiosulfonate ester, —(=O)$_2$S— (any silane with this functional group is a "thiosulfonate ester silane"); thiosulfate ester, —O—S(=O)$_2$ S— (any silane with this functional group is a "thiosulfate ester silane"); thiosulfamate ester, (—N—)S(=O)$_2$S— (any silane with this functional group is a "thiosulfamate ester silane"); thiosulfinate ester, —S(=O)S— (any silane with this functional group is a "thiosulfinate ester silane"); thiosulfite ester, —O—S(=O)S— (any silane with this functional group is a "thiosulfite ester silane"); thiosulfimate ester, (—N—)S(=O)—S— (any silane with this functional group is a "thiosulfimate ester silane"); thiophosphate ester, P(=O)(O—)$_2$(S—) (any silane with this functional group is a "thiophosphate ester silane"); dithiophosphate ester, P(=O)(O—)(S—)$_2$ or P(=S)(O—)$_2$(S—) (any silane with this functional group is a "dithiophosphate ester silane"); trithiophosphate ester, P(=O)(S—)$_3$ or P(=S)(O—)(S—)$_2$ (any silane with this functional group is a "trithiophosphate ester silane"); tetrathiophosphate ester P(=S)(S—)$_3$ (any silane with this functional group is a "tetrathiophosphate ester silane"); thiophosphamate ester, —P(=O)(—N—)(S—) (any silane with this functional group is a "thiophosphamate ester silane"); dithiophosphamate ester, —P(=S)(—N—)(S—) (any silane with this functional group is a "dithiophosphamate ester silane"); thiophosphoramidate ester, (—N—)P(=O)(O—)(S—)(any silane with this functional group is a "thiophosphoramidate ester silane"); dithiophosphoramidate ester, (—N—)P(=O)(S—)$_2$ or (—N—)P(=S)(O—)(S—)(any silane with this functional group is a "dithiophosphoramidate ester silane"); trithiophosphoramidate ester, (—N—)P(=S)(S—)$_2$ (any silane with this functional group is a "trithiophosphoramidate ester silane").

Novel silanes of the present invention are those wherein Y groups are —C(=NR)—; —SC(=NR)—; —SC(=O)—; —OC(=O)—, —S(=O)—; —S(=O)$_2$—; —OS(=O)$_2$—; —(NR)S(=O)$_2$—; —SS(=O)—; —OS(=O)—; —(NR)S(=O)—; —SS(=O)$_2$—; (—S)$_2$P(=O)—; —(—S)P(=O)—; —P(=O)(—)$_2$; (—S)$_2$P(=S)—; —(—S)P(=S)—; —P(=S)(—)$_2$; (—NR)$_2$P(=O)—; (—NR)(—S)P(=O)—; (—O)(—NR)P(=O)—; (—O)(—S)P(=O)—; (—O)$_2$p(=O)—; —(—O)P(=O)—; —(—NR)P(=O)—; (—NR)$_2$P(=S)—; (—NR)(—S)P(=S)—; —(O)(—NR)P(=S)—; (—O)(—S)P(=S)—; (—O)$_2$P(=S)—; —(—O)P(=S)—; and —(—NR)P(=S)—. Particularly preferred of these are —OC(=O)—; —SC(=O)—; —S(=O)—; —OS(=O)—; —(—S)P(=O)—; and —P(=O)(—)$_2$.

Another novel silane would be one wherein Y is —C(=O)— wherein G has a primary carbon attached to the carbonyl and is a $C_2$-$C_{12}$ alkyl, more preferably a $C_6$-$C_8$ alkyl.

Another preferred novel structure is of the form $X_3$SiGSC(=O)GC(=O)SGSi$X_3$ wherein G is a divalent hydrocarbon.

Examples of G include —(CH$_2$)$_n$— wherein n is 1 to 12, diethylene cyclohexane, 1,2,4-triethylene cyclohexane, and diethylene benzene. It is preferred that the sum of the carbon atoms within the G groups within the molecule are from 3 to 18, more preferably 6 to 14. This amount of carbon in the blocked mercaptosilane facilitates the dispersion of the inorganic filler into the organic polymers, thereby improving the balance of properties in the cured filled rubber.

Preferable R groups are alkyls of $C_1$ to $C_4$ and H.

Specific examples of X are methoxy, ethoxy, isobutoxy, propoxy, isopropoxy, acetoxy, and oximato. Methoxy, acetoxy, and ethoxy are preferred. At least one X must be reactive (i.e., hydrolyzable).

Preferred embodiments are wherein p is 0 to 2; X is RO— or RC(=O)O—; R is hydrogen, phenyl, isopropyl, cyclohexyl, or isobutyl; G is a substituted phenyl or substituted straight chain alkyl of $C_2$ to $C_{12}$. The most preferred embodiments include those wherein p is zero, X is ethoxy, and G is a $C_3$-$C_{12}$ alkyl derivative.

Representative examples of the silanes of the present invention include:

2-triethoxysilyl-1-ethyl thioacetate; 2-trimethoxysilyl-1-ethyl thioacetate;

2-(methyldimethoxysilyl)-1-ethyl thioacetate; 3-trimethoxysilyl-1-propyl thioacetate;

triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate;
methyldiisopropoxysilylmethyl thioacetate; dimethylethoxysilylmethyl thioacetate;
dimethylmethoxysilylmethyl thioacetate; dimethylisopropoxysilylmethyl thioacetate;
2-driisopropoxysilyl-1-ethyl thioacetate; 2-(methyldiethoxysilyl)-1-ethyl thioacetate;
2-(methyldiisopropoxysilyl)-1-ethyl thioacetate; 2-(dimethylethoxysilyl)-1-ethyl thioacetate;
2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate;
3-methyldiethoxysilyl-1-propyl thioacetate; 3-methyldimethoxysilyl-1-propyl thioacetate;
3-methyldiisopropoxysilyl-1-propyl thioacetate;
1-(2-triethoxysilyl-1-ethyl)-4-thioacetylcyclohexane;
1-(2-triethoxysilyl-1-ethyl)-3-thioacetylcyclohexane; 2-triethoxysilyl-5-thioacetylnorbornene;
2-triethoxysilyl-4-thioacetylnorbornene; 2-(2-triethoxysilyl-1-ethyl)-5-thioacetylnorbornene;
2-(2-triethoxysilyl-1-ethyl)-4-thioacetylnorbornene;
1-(1-oxo-2-thia-5-triethoxysilylpenyl)benzoic acid; 6-triethoxysilyl-1-hexyl thioacetate;
1-triethoxysilyl-5-hexyl thioacetate; 8-triethoxysilyl-1-octyl thioacetate;
1-triethoxysilyl-7-octyl thioacetate; 6-triethoxysilyl-1-hexyl thioacetate;
1-triethoxysilyl-5-octyl thioacetate; 8-trimethoxysilyl-1-octyl thioacetate;
1-trimethoxysilyl-7-octyl thioacetate; 10-triethoxysilyl-1-decyl thioacetate;
1-triethoxysilyl-9-decyl thioacetate; 1-triethoxysilyl-2-butyl thioacetate;
1-triethoxysilyl-3-butyl thioacetate; 1-triethoxysilyl-3-methyl-2-butyl thioacetate;
1-triethoxysilyl-3-methyl-3-butyl thioacetate; 3-trimethoxysilyl-1-propyl thiooctanoate;
3-triethoxysilyl-1-propyl thiopalmitate; 3-triethoxysilyl-1-propyl thiooctanoate;
3-triethoxysilyl-1-propyl thiobenzoate; 3-triethoxysilyl-1-propyl thio-2-ethylhexanoate;
3-methyldiacetoxysilyl-1-propyl thioacetate; 3-triacetoxysilyl-1-propyl thioacetate;
2-methyldiacetoxysilyl-1-ethyl thioacetate; 2-triacetoxysilyl-1-ethyl thioacetate;
1-methyldiacetoxysilyl-1-ethyl thioacetate; 1-triacetoxysilyl-1-ethyl thioacetate;
tris-(3-triethoxysilyl-1-propyl)trithiophosphate;
bis-(3-triethoxysilyl-1-propyl)methyldithiophosphonate;
bis-(3-triethoxysilyl-1-propyl)ethyldithiophosphonate;
3-thiethoxysilyl-1-propyldimethylthiophosphinate;
3-triethoxysilyl-1-propyldiethylthiophosphinate;
tris-(3-triethoxysilyl-1-propyl)tetrathiophosphate;
bis-(3-triethoxysilyl-1-propyl)methyltrithiophosphonate;
bis-(3-triethoxysilyl-1propyl)ethyltrithiophosphonate;
3-triethoxysilyl-1-propyldimethyldithiophosphinate;
3-triethoxysilyl-1-propyldiethyldithiophosphinate;
tris-(3-methyldimethoxysilyl-1-propyl)trithiophosphate;
bis-(3-methyldimethoxysilyl-1-propyl)methyldithiophosphonate;
bis-(3-methyldimethoxysilyl-1-propyl)ethyldithiophosphonate;
3-methyldimethoxysilyl-1-propyldimethylthiophosphinate;
3-methyldimethoxysilyl-1-propyldiethylthiophosphinate;
3-triethoxysilyl-1-propylmethylthiosulphate;
3-triethoxysilyl-1-propylmethanethiosulphonate;
3-triethoxysilyl-1-propylethanethiosulphonate;
3-triethoxysilyl-1-propylbenzenethiosulphonate;
3-triethoxysilyl-1-propyltoluenethiosulphonate;
3-triethoxysilyl-1-propylnaphthalenethiosulphonate;
3-triethoxysilyl-1-propylxylenethiosulphonate; triethoxysilylmethylmethylthiosulphate;
triethoxysilylmethylmethanethiosulphonate; triethoxysilylmethylethanethiosulphonate;
triethoxysilylmethylbenzenethiosulphonate; triethoxysilylmethyltoluenethiosulphonate;
triethoxysilylmethylnaphthalenethiosulphonate; and triethoxysilylmethylxylenethiosulphonate.

Mixtures of various blocked mercaptosilanes may be used, including wherein synthetic methods result in a distribution of various silanes or where mixes of blocked mercaptosilanes are used for their various blocking or leaving functionalities. Moreover, it is understood that the partial hydrolyzates of these blocked mercaptosilanes (i.e., blocked mercaptosiloxanes) may also be encompassed by the blocked mercaptosilanes herein, in that these partial hydrolyzates will be a side product of most methods of manufacture of the blocked mercaptosilane or can occur upon storage of the blocked mercaptosilane, especially in humid conditions.

The silane, if liquid, may be loaded on a carrier, such as a porous polymer, carbon black, or silica so that it is in solid form for delivery to the rubber. In a preferred mode, the carrier would be part of the inorganic filler to be used in the rubber.

Manufacture of Silanes

The methods of preparation for blocked mercaptosilanes can involve esterification of sulfur in a sulfur-containing silane and direct incorporation of the thioester group into a silane, either by substitution of an appropriate leaving group or by addition across a carbon-carbon double bond. Illustrative examples of synthetic procedures for the preparation of thioester silanes would include: Reaction 1) the reaction between a mercaptosilane and an acid anhydride corresponding to the thioester group present in the desired product; Reaction 2) reaction of an alkali metal salt of a mercaptosilane with the appropriate acid anhydride or acid halide; Reaction 3) the transesterification between a mercaptosilane and an ester, optionally using any appropriate catalyst such as an acid, base, tin compound, titanium compound, transition metal salt, or a salt of the acid corresponding to the ester; Reaction 4) the transesterification between a thioester silane and another ester, optionally using any appropriate catalyst such as an acid, base, tin compound, titanium compound, transition metal salt, or a salt of the acid corresponding to the ester; Reaction 5) the transesterification between a 1-sila-2-thiacyclopentane or a 1-sila-2-thiacyclohexane and an ester, optionally using any appropriate catalyst such as an acid, base, tin compound, titanium compound, transition metal salt, or a salt of the acid corresponding to the ester; Reaction 6) the free radical addition of a thioacid across a carbon-carbon double bond of an alkene-functional silane, catalyzed by UV light, heat, or the appropriate free radical initiator wherein, if the thioacid is a thiocarboxylic acid, the two reagents are brought into contact with each other in such a way as to ensure that whichever reagent is added to the other is reacted substantially before the addition proceeds; and Reaction 7) the reaction between an alkali metal salt of a thioacid with a haloalkylsilane.

Acid halides include but are not limited to, in addition to organic acid halides, inorganic acid halides, such as $POT_3$, $SOT_2$, $SO_2T_2$, $COT_2$, $CST_2$, $PST_3$ and $PT_3$, wherein T is a halide. Acid anhydrides include but are not limited to, in addition to organic acid anhydrides (and their sulfur analogs), inorganic acid anhydrides such as $SO_3$, $SO_2$, $P_2O_5$, $P_2S$ $H_2S_2O_7$, $CO_2$, COS, and $CS_2$.

Illustrative examples of synthetic procedures for the preparation of thiocarboxylate-functional silanes would include: Reaction 8) the reaction between a mercaptosilane and a carboxylic acid anhydride corresponding to the thiocarboxylate group present in the desired product; Reaction 9) reaction of an alkali metal salt of a mercaptosilane with the appropriate carboxylic acid anhydride or acid halide; Reaction 10) the transesterification between a mercaptosilane and a carboxylate ester, optionally using any appropriate catalyst, such as an acid, base, tin compound, titanium compound, transition metal salt, or a salt of the acid corresponding to the carboxylate ester; Reaction 11) the transesterification between a thiocarboxylate-functional silane and another ester, optionally using any appropriate catalyst, such as an acid, base, tin compound, titanium compound, transition metal salt, or a salt of the acid corresponding to the other ester; Reaction 12) the transesterification between a 1-sila-2-thiacyclopentane or a 1-sila-2-thiacyclohexane and a carboxylate ester, optionally using any appropriate catalyst, such as an acid, base, tin compound, titanium compound, transition metal salt, or a salt of the acid corresponding to the carboxylate ester; Reaction 13) the free radical addition of a thiocarboxylic acid across a carbon-carbon double bond of an alkene-functional silane, catalyzed by UV light, heat, or the appropriate free radical initiator; and Reaction 14) the reaction between an alkali metal salt of a thiocarboxylic acid with a haloalkylsilane.

Reactions 1 and 8 can be carried out by distilling a mixture of the mercaptosilane and the acid anhydride and optionally a solvent. Appropriate boiling temperatures of the mixture are in the range of 60° to 200° C.; preferably 70° to 170° C; optionally 50° to 250° C. This process leads to a chemical reaction in which the mercapto group of the mercaptosilane is esterified to the thioester silane analog with release of an equivalent of the corresponding acid. The acid typically is more volatile than the acid anhydride. The reaction is driven by the removal of the more volatile acid by distillation. For the more volatile acid anhydrides, such as acetic anhydride, the distillation preferably is carried out at ambient pressure to reach temperatures sufficient to drive the reaction toward completion. For less volatile materials, solvents such as toluene, xylene, glyme, and diglyme could be used with the process to limit temperature. Alternatively, the process could be run at reduced pressure. It would be useful to use up to a twofold excess or more of the acid anhydride which would be distilled out of the mixture after all of the more volatile reaction coproducts, consisting of acids and nonsilane esters, have been distilled out. This excess of acid anhydride would serve to drive the reaction to completion, as well as to help drive the coproducts out of the reaction mixture. At the completion of the reaction, distillation should be continued to drive out the remaining acid anhydride. The product optionally could be distilled.

Reactions 2 and 9 can be carried out in two steps. The first step would involve conversion of the mercaptosilane to a corresponding metal derivative. Alkali metal derivatives, especially sodium or also potassium and lithium, are preferable. The metal derivative would be prepared by adding the alkali metal or a strong base derived from the alkali metal to the mercaptosilane. The reaction would occur at ambient temperature. Appropriate bases would include alkali metal alkoxides, amides, hydrides, and mercaptides. Alkali metal organometallic reagents would also be effective. Grignard reagents would yield magnesium derivatives, which would be another alternative. Solvents, such as toluene, xylene, benzene, aliphatic hydrocarbons, ethers, and alcohols could be used to prepare the alkali metal derivatives. Once the alkali metal derivative is prepared, any alcohol present would need to be removed. This could be done by distillation or evaporation. Alcohols, such as methanol, ethanol, propanol, isopropanol, butanol, isobutanol, and t-butanol may be removed by azeotropic distillation with benzene, toluene, xylene, or aliphatic hydrocarbons. Toluene and xylene are preferable; toluene is most preferable. The second step in the overall process would be to add to this solution, with stirring, the acid chloride or acid anhydride at temperatures between −20° C. and the boiling point of the mixture, preferably at temperatures between 0° C. and ambient temperature. The product would be isolated by removing the salt and solvent. It could be purified by distillation.

Reactions 3 and 10 could be carried out by distilling a mixture of the mercaptosilane and the ester and optionally a solvent and/or a catalyst. Appropriate boiling temperatures of the mixture would be above 100° C. This process leads to a chemical reaction in which the mercapto group of the mercaptosilane is esterified to the thioester silane analog with release of an equivalent of the corresponding alcohol. The reaction is driven by the removal of the alcohol by distillation, either as the more volatile species, or as an azeotrope with the ester. For the more volatile esters the distillation is suitably carried out at ambient pressure to reach temperatures sufficient to drive the reaction toward completion. For less volatile esters, solvents, such as toluene, xylene, glyme, and diglyme could be used with the process to limit temperature. Alternatively, the process could be run at reduced pressure. It is useful to use up to a twofold excess or more of the ester, which would be distilled out of the mixture after all of the alcohol coproduct has been distilled out. This excess ester would serve to drive the reaction to completion as well as to help drive the coproduct alcohol out of the reaction mixture. At the completion of the reaction, distillation would be continued to drive out the remaining ester. The product optionally could be distilled.

Reactions 4 and 11 could be carried out by distilling a mixture of the thioester silane and the other ester and optionally a solvent and/or a catalyst. Appropriate boiling temperatures of the mixture would be above 80° C.; preferably above 100° C. The temperature would preferably not exceed 250° C. This process leads to a chemical reaction in which the thioester group of the thioester silane is transesterified to a new thioester silane with release of an equivalent of a new ester. The new thioester silane generally would be the least volatile species present; however, the new ester would be more volatile than the other reactants. The reaction would be driven by the removal of the new ester by distillation. The distillation can be carried out at ambient pressure to reach temperatures sufficient to drive the reaction toward completion. For systems containing only less volatile materials, solvents, such as toluene, xylene, glyme, and diglyme could be used with the process to limit temperature. Alternatively, the process could be run at reduced pressure. It would be useful to use up to a twofold excess or more of the other ester, which would be distilled out of the mixture after all of the new ester coproduct has been distilled out. This excess other ester would serve to drive the reaction to completion as well as to help drive the coproduct other ester out of the reaction mixture. At the completion of the reaction, distillation would be continued to drive out the remaining said new ester. The product optionally then could be distilled.

Reactions 5 and 12 could be carried out by heating a mixture of the 1-sila-2-thiacyclopentane or the 1-sila-2-thiacyclohexane and the ester with the catalyst. Optionally, the mixture could be heated or refluxed with a solvent, preferably a solvent whose boiling point matches the desired temperature. Optionally a solvent of higher boiling point than the desired reaction temperature can be used at reduced pressure, the pressure being adjusted to bring the boiling point down to the desired reaction temperature. The temperature of the mixture would be in the range of 80° to 250° C.; preferably 100° to 200° C. Solvents, such as toluene, xylene, aliphatic hydrocarbons, and diglyme could be used with the process to adjust the temperature. Alternatively, the process could be run under reflux at reduced pressure. The most preferable condition is to heat a mixture of the 1-sila-2-thiacyclopentane or the 1-sila-2-thiacyclohexane and the ester, without solvent, preferably under inert atmosphere, for a period of 20 to 100 hours at a temperature of 120° to 170° C. using the sodium, potassium, or lithium salt of the acid corresponding to the ester as a catalyst. The process leads to a chemical reaction in which the sulfur-silicon bond of the 1-sila-2-thiacyclopentane or the 1-sila-2-thiacyclohexane is transesterified by addition of the ester across said sulfur-silicon bond. The product is the thioester silane analog of the original 1-sila-2-thiacyclopentane or the 1-sila-2-thiacyclohexane. Optionally, up to a twofold excess or more of the ester would be used to drive the reaction toward completion. At the completion of the reaction, the excess ester can be removed by distillation. The product optionally could be purified by distillation.

Reactions 6 and 13 can be carried out by heating or refluxing a mixture of the alkene-functional silane and the thioacid. Aspects of Reaction 13 have been disclosed previously in U.S. Pat. No. 3,692,812 and by G. A. Gornowicz et al., in J. Org. Chem. (1968), 33(7), 2918-24. The uncatalyzed reaction can occur at temperatures as low as 105° C., but often fails. The probability of success increases with temperature and becomes high when the temperature exceeds 160° C. The reaction may be made reliable and the reaction brought largely to completion by using UV radiation or a catalyst. With a catalyst, the reaction can be made to occur at temperatures below 90° C. Appropriate catalysts are free radical initiators, e.g., peroxides, preferably organic peroxides, and azo compounds. Examples of peroxide initiators include peracids, such as perbenzoic and peracetic acids; esters of peracids; hydroperoxides, such as t-butyl hydroperoxide; peroxides, such as di-t-butyl peroxide; and peroxy-acetals and ketals, such as 1,1-bis(t-butylperoxy) cyclohexane, or any other peroxide. Examples of azo initiators include azobisisobutyronitrile (AIBN), 1,1-azobis (cyclohexanecarbonitrile) (VAZO, DuPont product); and azo-tert-butane. The reaction can be run by heating a mixture of the alkene-functional silane and the thioacid with the catalyst. It is preferable for the overall reaction to be run on an equimolar or near equimolar basis to get the highest conversions. The reaction is sufficiently exothermic that it tends to lead to a rapid temperature increase to reflux followed by a vigorous reflux as the reaction initiates and continues rapidly. This vigorous reaction can lead to hazardous boil-overs for larger quantities. Side reactions, contamination, and loss in yield can result as well from uncontrolled reactions. The reaction can be controlled effectively by adding partial quantities of one reagent to the reaction mixture, initiating the reaction with the catalyst, allowing the reaction to run its course largely to completion, and then adding the remains of the reagent, either as a single addition or as multiple additives. The initial concentrations and rate of addition and number of subsequent additions of the deficient reagent depend on the type and amount of catalyst used, the scale of the reaction, the nature of the starting materials, and the ability of the apparatus to absorb and dissipate heat. A second way of controlling the reaction would involve the continuous addition of one reagent to the other with concomitant continuous addition of catalyst. Whether continuous or sequential addition is used, the catalyst can be added alone and/or preblended with one or both reagents or combinations thereof. Two methods are preferred for reactions involving thiolacetic acid and alkene-functional silanes containing terminal carbon-carbon double bonds. The first involves initially bringing the alkene-functional silane to a temperature of 160° to 180° C., or to reflux, whichever temperature is lower. The first portion of thiolacetic acid is added at a rate as to maintain up to a vigorous, but controlled, reflux. For alkene-functional silanes with boiling points above 100° to 120° C., this reflux results largely from the relatively low boiling point of thiolacetic acid (88° to 92° C., depending on purity) relative to the temperature of the alkene-functional silane. At the completion of the addition, the reflux rate rapidly subsides. It often accelerates again within several minutes, especially if an alkene-functional silane with a boiling point above 120° C. is used, as the reaction initiates. If it does not initiate within 10 to 15 minutes, initiation can be brought about by addition of catalyst. The preferred catalyst is di-t-butyl peroxide. The appropriate quantity of catalyst is from 0.2 to 2 percent, preferably from 0.5 to 1 percent, of the total mass of mixture to which the catalyst is added. The reaction typically initiates within a few minutes as evidenced by an increase in reflux rate. The reflux temperature gradually increases as the reaction proceeds. Then the next portion of thiolacetic acid is added, and the aforementioned sequence of steps is repeated. The preferred number of thiolacetic additions for total reaction quantities of about one to about four kilograms is two, with about one-third of the total thiolacetic acid used in the first addition and the remainder in the second. For total quantities in the range of about four to ten kilograms, a total of three thiolacetic additions is preferred, the distribution being approximately 20 percent of the total used in the first addition, approximately 30 percent in the second addition, and the remainder in the third addition. For larger scales involving thiolacetic acid and alkene-functional silanes, it is preferable to use more than a total of three thiolacetic additions and, more preferably, to add the reagents in the reverse order. Initially, the total quantity of thiolacetic acid is brought to reflux. This is followed by continuous addition of the alkene-functional silane to the thiolacetic acid at such a rate as to bring about a smooth but vigorous reaction rate. The catalyst, preferably di-t-butylperoxide, can be added in small portions during the course of the reaction or as a continuous flow. It is best to accelerate the rate of catalyst addition as the reaction proceeds to completion to obtain the highest yields of product for the lowest amount of catalyst required. The total quantity of catalyst used should be 0.5 to 2 percent of the total mass of reagents used. Whichever method is used, the reaction is followed up by a vacuum stripping process to remove volatiles and unreacted thiolacetic acid and silane. The product may be purified by distillation.

Methods to run Reactions 7 and 14 can be carried out in two steps. The first step involves preparation of a salt of the thioacid. Alkali metal derivatives are preferred, with the sodium derivative being most preferred. These salts would be prepared as solutions in solvents in which the salt is appreciably soluble, but suspensions of the salts as solids in solvents in which the salts are only slightly soluble are also a viable option. Alcohols, such as propanol, isopropanol, butanol, isobutanol, and t-butanol, and preferably methanol and ethanol are useful because the alkali metal salts are slightly soluble in them. In cases where the desired product is an alkoxysilane, it is preferable to use an alcohol corresponding to the silane alkoxy group to prevent transesterification at the silicon ester. Alternatively, nonprotic solvents can be used. Examples of appropriate solvents are ethers or polyethers such as glyme, diglyme, and dioxanes; N,N-dimethylformamide; N,N-dimethylacetamide; dimethylsulfoxide; N-methylpyrrolidinone; or hexamethylphosphoramide. Once a solution, suspension, or combination thereof of the salt of the thioacid has been prepared, the second step is to react it with the appropriate haloalkylsilane. This may be accomplished by stirring a mixture of the haloalkylsilane with the solution, suspension, or combination thereof of the salt of the thioacid at temperatures corresponding to the liquid range of the solvent for a period of time sufficient to complete substantially the reaction. Preferable temperatures are those at which the salt is appreciably soluble in the solvent and at which the reaction proceeds at an acceptable rate without excessive side reactions. With reactions starting from chloroalkylsilanes in which the chlorine atom is not allylic or benzylic, preferable temperatures are in the range of 60° to 160° C. Reaction times can range from one or several hours to several days. For alcohol solvents where the alcohol contains four carbon atoms or fewer, the most preferred temperature is at or near reflux. When diglyme is used as a solvent, the most preferred temperature is in the range of 70° to 120° C., depending on the thioacid salt used. If the haloalkylsilane is a bromoalkylsilane or a chloroalkylsilane in which the chlorine atom is allylic or benzylic, temperature reductions of 30° to 60° C. are appropriate relative to those appropriate for nonbenzylic or nonallylic chloroalkylsilanes because of the greater reactivity of the bromo group. Bromoalkylsilanes are preferred over chloroalkylsilanes because of their greater reactivity, lower temperatures required, and greater ease in filtration or centrifugation of the coproduct alkali metal halide. This preference, however, can be overridden by the lower cost of the chloroalkylsilanes, especially for those containing the halogen in the allylic or benzylic position. For reactions between straight chain chloroalkylethoxysilanes and sodium thiocarboxylates to form thiocarboxylate ester ethoxysilanes, it is preferable to use ethanol at reflux for 10 to 20 hours if 5 to 20 percent mercaptosilane is acceptable in the product. Otherwise, diglyme would be an excellent choice, in which the reaction would be run preferably in the range of 80° to 120° C. for one to three hours. Upon completion of the reaction the salts and solvent should be removed, and the product may be distilled to achieve higher purity.

If the salt of the thioacid to be used in Reactions 7 and 14 is not commercially available, its preparation may be accomplished by one of two methods, described below as Method A and Method B. Method A involves adding the alkali metal or a base derived from the alkali metal to the thioacid. The reaction occurs at ambient temperature. Appropriate bases include alkali metal alkoxides, hydrides, carbonates, and bicarbonates. Solvents, such as toluene, xylene, benzene, aliphatic hydrocarbons, ethers, and alcohols may be used to prepare the alkali metal derivatives. In Method B, acid chlorides or acid anhydrides would be converted directly to the salt of the thioacid by reaction with the alkali metal sulfide or hydrosulfide. Hydrated or partially hydrous alkali metal sulfides or hydrosulfides are available; however, anhydrous or nearly anhydrous alkali metal sulfides or hydrosulfides are preferred. Hydrous materials can be used, however, but with loss in yield and hydrogen sulfide formation as a coproduct. The reaction involves addition of the acid chloride or acid anhydride to the solution or suspension of the alkali metal sulfide and/or hydrosulfide and heating at temperatures ranging from ambient to the reflux temperature of the solvent for a period of time sufficient largely to complete the reaction, as evidenced by the formation of the coproduct salts.

If the alkali metal salt of the thioacid is prepared in such a way that an alcohol is present, either because it was used as a solvent, or because it formed, as for example, by the reaction of a thioacid with an alkali metal alkoxide, it may be desirable to remove the alcohol if a product low in mercaptosilane is desired. In this case, it would be necessary to remove the alcohol prior to reaction of the salt of the thioacid with the haloalkylsilane. This could be done by distillation or evaporation. Alcohols, such as methanol, ethanol, propanol, isopropanol, butanol, isobutanol, and t-butanol are preferably removed by azeotropic distillation with benzene, toluene, xylene, or aliphatic hydrocarbons. Toluene and xylene are preferred.

Utility

The blocked mercaptosilanes described herein are useful as coupling agents for organic polymers (i.e., rubbers) and inorganic fillers. The blocked mercaptosilanes are unique in that the high efficiency of the mercapto group can be utilized without the detrimental side effects typically associated with the use of mercaptosilanes, such as high processing viscosity, less than desirable filler dispersion, premature curing (scorch), and odor. These benefits are accomplished because the mercaptan group initially is nonreactive because of the blocking group. The blocking group substantially prevents the silane from coupling to the organic polymer during the compounding of the rubber. Generally, only the reaction of the silane —$SiX_3$ group with the filler can occur at this stage of the compounding process. Thus, substantial coupling of the filler to the polymer is precluded during mixing, thereby minimizing the undesirable premature curing (scorch) and the associated undesirable increase in viscosity. One can achieve better cured filled rubber properties, such as a balance of high modulus and abrasion resistance, because of the avoidance of premature curing.

In use, one or more of the blocked mercaptosilanes are mixed with the organic polymer before, during, or after the compounding of the filler into the organic polymer. It is preferred to add the silanes before or during the compounding of the filler into the organic polymer, because these silanes facilitate and improve the dispersion of the filler. The total amount of silane present in the resulting combination should be about 0.05 to about 25 parts by weight per hundred parts by weight of organic polymer (phr), more preferably 1 to 10 phr. Fillers can be used in quantities ranging from about 5 to 100 phr, more preferably from 25 to 80 phr.

When reaction of the mixture to couple the filler to the polymer is desired, a deblocking agent is added to the mixture to deblock the blocked mercaptosilane. The deblocking agent may be added at quantities ranging from about 0.1 to about 5 phr, more preferably in the range of from 0.5 to 3 phr. If alcohol or water is present (as is common) in the mixture, a catalyst (e.g., tertiary amines, Lewis acids, or thiols) may be used to initiate and promote the loss of the blocking group by hydrolysis or alcoholysis to liberate the corresponding mercaptosilane. Alternatively, the deblocking agent may be a nucleophile containing a hydrogen atom sufficiently labile such that the hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile containing the original blocking group. This transfer of the blocking group from the silane to the nucleophile could be driven, for example, by a greater thermodynamic stability of the products (mercaptosilane and nucleophile containing the blocking group) relative to the initial reactants (blocked mercaptosilane and nucleophile). For example, if the nucleophile were an amine containing an N—H bond, transfer of the blocking group from the blocked mercaptosilane would yield the mercaptosilane and one of several classes of amides corresponding to the type of blocking group used. For example, carboxyl blocking groups deblocked by amines would yield amides, sulfonyl blocking groups deblocked by amines would yield sulfonamides, sulfinyl blocking groups deblocked by amines would yield sulfinamides, phosphonyl blocking groups deblocked by amines would yield phosphonamides, phosphinyl blocking groups deblocked by amines would yield phosphinamides. What is important is that regardless of the blocking group initially present on the blocked mercaptosilane and regardless of the deblocking agent used, the initially substantially inactive (from the standpoint of coupling to the organic polymer) blocked mercaptosilane is substantially converted at the desired point in the rubber compounding procedure to the active mercaptosilane. It is noted that partial amounts of the nucleophile may be used (i.e., a stoichiometric deficiency), if one were to deblock only part of the blocked mercaptosilane to control the degree of vulcanization of a specific formulation.

Water typically is present on the inorganic filler as a hydrate, or bound to a filler in the form of a hydroxyl group. The deblocking agent could be added in the curative package or, alternatively, at any other stage in the compounding process as a single component. Examples of nucleophiles would include any primary or secondary amines, or amines containing C=N double bonds, such as imines or guanidines, with the proviso that said amine contains at least one N—H (nitrogen-hydrogen) bond. Numerous specific examples of guanidines, amines, and imines well known in the art, which are useful as components in curatives for rubber, are cited in J. Van Alphen, *Rubber Chemicals*, (Plastics and Rubber Research Institute TNO, Delft, Holland, 1973). Some examples include N,N'-diphenylguanidine, N,N',N"-triphenylguanidine, N,N'-di-ortho-tolylguanidine, orthobiguanide, hexamethylenetetramine, cyclohexylethylamine, dibutylamine, and 4,4'-diaminodiphenylmethane. Any general acid catalysts used to transesterify esters, such as Bronsted or Lewis acids, could be used as catalysts.

The rubber composition need not be, but preferably is, essentially free of functionalized siloxanes, especially those of the type disclosed in Australian Patent AU-A-10082/97, which is incorporated herein by reference. Most preferably, the rubber composition is free of functionalized siloxanes.

In practice, sulfur vulcanized rubber products typically are prepared by thermomechanically mixing rubber and various ingredients in a sequentially stepwise manner followed by shaping and curing the compounded rubber to form a vulcanized product. First, for the aforesaid mixing of the rubber and various ingredients, typically exclusive of sulfur and sulfur vulcanization accelerators (collectively "curing agents"), the rubber(s) and various rubber compounding ingredients typically are blended in at least one, and often (in the case of silica filled low rolling resistance tires) two, preparatory thermomechanical mixing stage(s) in suitable mixers. Such preparatory mixing is referred to as nonproductive mixing or nonproductive mixing steps or stages. Such preparatory mixing usually is conducted at temperatures up to 140° to 200° C. and often up to 150° to 180° C. Subsequent to such preparatory mix stages, in a final mixing stage, sometimes referred to as a productive mix stage, deblocking agent (in the case of this invention), curing agents, and possibly one or more additional ingredients are mixed with the rubber compound or composition, typically at a temperature in a range of 50° to 130° C., which is a lower temperature than the temperatures utilized in the preparatory mix stages to prevent or retard premature curing of the sulfur curable rubber, which is sometimes referred to as scorching of the rubber composition. The rubber mixture, sometimes referred to as a rubber compound or composition, typically is allowed to cool, sometimes after or during a process intermediate mill mixing, between the aforesaid various mixing steps, for example, to a temperature of about 50° C. or lower. When it is desired to mold and to cure the rubber, the rubber is placed into the appropriate mold at about at least 130° C. and up to about 200° C., which will cause the vulcanization of the rubber by the mercapto groups on the mercaptosilane and any other free sulfur sources in the rubber mixture.

By thermomechanical mixing, it is meant that the rubber compound, or composition of rubber and rubber compounding ingredients, is mixed in a rubber mixture under high shear conditions where it autogenously heats up as a result of the mixing primarily due to shear and associated friction within the rubber mixture in the rubber mixer. Several chemical reactions may occur at various steps in the mixing and curing processes.

The first reaction is a relatively fast reaction and is considered herein to take place between the filler and the $SiX_3$ group of the blocked mercaptosilane. Such reaction may occur at a relatively low temperature such as, for example, at about 120° C. The second and third reactions are considered herein to be the deblocking of the mercaptosilane and the reaction which takes place between the sulfuric part of the organosilane (after deblocking), and the sulfur vulcanizable rubber at a higher temperature, for example, above about 140° C.

Another sulfur source may be used, for example, in the form of elemental sulfur as $S_8$. A sulfur donor is considered herein as a sulfur containing compound which liberates free, or elemental, sulfur at a temperature in a range of 140° to 190° C. Examples of such sulfur donors may be, but are not limited to, polysulfide vulcanization accelerators and organosilane polysulfides with at least two connecting sulfur atoms in its polysulfide bridge. The amount of free sulfur source addition to the mixture can be controlled or manipulated as a matter of choice relatively independently from the addition of the aforesaid blocked mercaptosilane. Thus, for example, the independent addition of a sulfur source may be manipulated by the amount of addition thereof and by sequence of addition relative to addition of other ingredients to the rubber mixture.

Addition of an alkyl silane to the coupling agent system (blocked mercaptosilane plus additional free sulfur source and/or vulcanization accelerator) typically in a mole ratio of alkyl silane to blocked mercaptosilane in a range of 1/50 to 1/2 promotes an even better control of rubber composition processing and aging.

A rubber composition is prepared by a process which comprises the sequential steps of:

(A) thermomechanically mixing, in at least one preparatory mixing step, to a temperature of 140° to 200° C., alternatively to 140° to 190° C., for a total mixing time of 2 to 20 minutes, alternatively 4 to 15 minutes, for such mixing step(s);

(i) 100 parts by weight of at least one sulfur vulcanizable rubber selected from conjugated diene homopolymers and copolymers, and copolymers of at least one conjugated diene and aromatic vinyl compound, (ii) 5 to 100 phr (parts per hundred rubber), preferably 25 to 80 phr, of particulate filler, wherein preferably the filler contains 1 to 85 weight percent carbon black, (iii) 0.05 to 20 parts by weight filler of at least one blocked mercaptosilane;

(B) subsequently blending therewith, in a final thermomechanical mixing step at a temperature to 50° to 130° C for a time sufficient to blend the rubber, preferably between 1 to 30 minutes, more preferably 1 to 3 minutes, at least one deblocking agent at about 0.05 to 20 parts by weight of the filler and a curing agent at 0 to 5 phr; and optionally (C) curing said mixture at a temperature of 130° to 200° C. for about 5 to 60 minutes.

The process may also comprise the additional steps of preparing an assembly of a tire or sulfur vulcanizable rubber with a tread comprised of the rubber composition prepared according to this invention and vulcanizing the assembly at a temperature in a range of 130° to 200° C.

Suitable organic polymers and fillers are well known in the art and are described in numerous texts, of which two examples include *The Vanderbilt Rubber Handbook*, R. F. Ohm, ed. (R. T. Vanderbilt Company, Inc., Norwalk, Conn., 1990), and *Manual for the Rubber Industry*, T. Kempermann, S. Koch, and J. Sumner, eds. (Bayer AG, Leverkusen, Germany, 1993). Representative examples of suitable polymers include solution styrene-butadiene rubber (sSBR), styrene-butadiene rubber (SBR), natural rubber (NR), polybutadiene (BR), ethylene-propylene co- and ter-polymers (EP, EPDM), and acrylonitrile-butadiene rubber (NBR). The rubber composition is comprised of at least one diene-based elastomer, or rubber. Suitable conjugated dienes are isoprene and 1,3-butadiene and suitable vinyl aromatic compounds are styrene and alpha methyl styrene. Thus, the rubber is a sulfur curable rubber. Such diene based elastomer, or rubber, may be selected, for example, from at least one of cis-1,4-polyisoprene rubber (natural and/or synthetic, and preferably natural rubber), emulsion polymerization prepared styrene/butadiene copolymer rubber, organic solution polymerization prepared styrene/butadiene rubber, 3,4-polyisoprene rubber, isoprene/butadiene rubber, styrene/isoprene/butadiene terpolymer rubber, cis-1,4-polybutadiene, medium vinyl polybutadiene rubber (35 percent to 50 percent vinyl), high vinyl polybutadiene rubber (50 percent to 75 percent vinyl), styrene/isoprene copolymers, emulsion polymerization prepared styrene/butadiene/acrylonitrile terpolymer rubber and butadiene/acrylonitrile copolymer rubber. An emulsion polymerization derived styrene/butadiene (eSBR) might be used having a relatively conventional styrene content of 20 percent to 28 percent bound styrene or, for some applications, an eSBR having a medium to relatively high bound styrene content, namely, a bound styrene content of 30 percent to 45 percent. Emulsion polymerization prepared styrenelbutadiene/acrylonitrile terpolymer rubbers containing 2 to 40 weight percent bound acrylonitrile in the terpolymer are also contemplated as diene based rubbers for use in this invention.

The solution polymerization prepared SBR (sSBR) typically has a bound styrene content in a range of 5 to 50 percent, preferably 9 to 36 percent. Polybutadiene elastomer may be conveniently characterized, for example, by having at least a 90 weight percent cis-1,4-content.

Representative examples of suitable filler materials include metal oxides, such as silica (pyrogenic and precipitated), titanium dioxide, aluminosilicate and alumina, siliceous materials including clays and talc, and carbon black. Particulate, precipitated silica is also sometimes used for such purpose, particularly when the silica is used in connection with a silane. In some cases, a combination of silica and carbon black is utilized for reinforcing fillers for various rubber products, including treads for tires. Alumina can be used either alone or in combination with silica. The term "alumina" can be described herein as aluminum oxide, or $Al_2O_3$. The fillers may be hydrated or in anhydrous form. Use of alumina in rubber compositions can be shown, for example, in U.S. Pat. No. 5,116,886 and EP 631,982.

The blocked mercaptosilane may be premixed, or prereacted, with the filler particles or added to the rubber mix during the rubber and filler processing, or mixing stage. If the silane and filler are added separately to the rubber mix during the rubber and filler mixing, or processing stage, it is considered that the blocked mercaptosilane then combines in situ with the filler.

The vulcanized rubber composition should contain a sufficient amount of filler to contribute a reasonably high modulus and high resistance to tear. The combined weight of the filler may be as low as about 5 to 100 phr, but is more preferably from 25 phr to 85 phr.

Precipitated silicas are preferred as the filler. The silica may be characterized by having a BET surface area, as measured using nitrogen gas, preferably in the range of 40 to 600 $m^2/g$, and more usually in a range of 50 to 300 $m^2/g$. The silica typically may also be characterized by having a dibutylphthalate (DBP) absorption value in a range of 100 to 350, and more usually 150 to 300. Further, the silica, as well as the aforesaid alumina and aluminosilicate, may be expected to have a CTAB surface area in a range of 100 to 220. The CTAB surface area is the external surface area as evaluated by cetyl trimethylammonium bromide with a pH of 9. The method is described in ASTM D 3849.

Mercury porosity surface area is the specific surface area determined by mercury porosimetry. For such technique, mercury is penetrated into the pores of the sample after a thermal treatment to remove volatiles. Set up conditions may be suitably described as using a 100 mg sample, removing volatiles during two hours at 105° C. and ambient atmospheric pressure, ambient to 2000 bars pressure measuring range. Such evaluation may be performed according to the method described in Winslow, Shapiro in ASTM bulletin, page 39 (1959) or according to DIN 66133. For such an evaluation, a CARLO-ERBA Porosimeter 2000 might be used. The average mercury porosity specific surface area for the silica should be in a range of 100 to 300 m²/g.

A suitable pore size distribution for the silica, alumina, and aluminosilicate according to such mercury porosity evaluation is considered herein to be:

5 percent or less of its pores have a diameter of less than about 10 nm; 60 percent to 90 percent of its pores have a diameter of 10 to 100 nm; 10 percent to 30 percent of its pores have a diameter of 100 to 1,000 nm; and 5 percent to 20 percent of its pores have a diameter of greater than about 1,000 nm.

The silica might be expected to have an average ultimate particle size, for example, in the range of 0.01 to 0.05 µm as determined by the electron microscope, although the silica particles may be even smaller, or possibly larger, in size. Various commercially available silicas may be considered for use in this invention such as, from PPG Industries under the HI-SIL trademark with designations HI-SIL 210, 243, etc.; silicas available from Rhone-Poulenc, with, for example, designation of ZEOSIL 1165MP; silicas available from Degussa with, for example, designations VN2 and VN3, etc.; and silicas commercially available from Huber having, for example, a designation of HUBERSIL 8745.

Where it is desired for the rubber composition, which contains both a siliceous filler such as silica, alumina and/or aluminosilicates and also carbon black reinforcing pigments, to be primarily reinforced with silica as the reinforcing pigment, it is often preferable that the weight ratio of such siliceous fillers to carbon black is at least 3/1 and preferably at least 10/1 and, thus, in a range of 3/1 to 30/1. The filler may be comprised of 15 to 95 weight percent precipitated silica, alumina, and/or aluminosilicate and, correspondingly 5 to 85 weight percent carbon black, wherein the carbon black has a CTAB value in a range of 80 to 150. Alternatively, the filler can be comprised of 60 to 95 weight percent of said silica, alumina, and/or aluminosilicate and, correspondingly, 40 to 5 weight percent carbon black. The siliceous filler and carbon black may be preblended or blended together in the manufacture of the vulcanized rubber.

The rubber composition may be compounded by methods known in the rubber compounding art, such as mixing the various sulfur-vulcanizable constituent rubbers with various commonly used additive materials. Examples of such commonly used additive materials include curing aids, such as sulfur, activators, retarders and accelerators, processing additives, such as oils, resins including tackifying resins, silicas, plasticizers, fillers, pigments, fatty acid, zinc oxide, waxes, antioxidants and antiozonants, peptizing agents, and reinforcing materials, such as, for example, carbon black. Depending on the intended use of the sulfur vulcanizable and sulfur vulcanized material (rubbers), the additives mentioned above are selected and commonly used in conventional amounts.

The vulcanization may be conducted in the presence of an additional sulfur vulcanizing agent. Examples of suitable sulfur vulcanizing agents include, for example, elemental sulfur (free sulfur) or sulfur donating vulcanizing agents, for example, an amino disulfide, polymeric polysulfide, or sulfur olefin adducts which are conventionally added in the final, productive, rubber composition mixing step. The sulfur vulcanizing agents (which are common in the art) are used, or added in the productive mixing stage, in an amount ranging from 0.4 to 3 phr, or even, in some circumstances, up to about 8 phr, with a range of from 1.5 to 2.5 phr, sometimes from 2 to 2.5 phr, being preferred.

Vulcanization accelerators, i.e., additional sulfur donors, may be used herein. It is appreciated that they may be, for example, of the type such as, for example, benzothiazole, alkyl thiuram disulfide, guanidine derivatives, and thiocarbamates. Representative of such accelerators are, for example, but are not limited to, mercapto benzothiazole, tetramethyl thiuram disulfide, benzothiazole disulfide, diphenylguanidine, zinc dithiocarbamate, alkylphenoldisulfide, zinc butyl xanthate, N-dicyclohexyl-2-benzothiazolesulfenamide, N-cyclohexyl-2-benzothiazolesulfenamide, N-oxydiethylenebenzothiazole-2-sulfenamide, N,N-diphenylthiourea, dithiocarbamylsulfenamide, N,N-diisopropylbenzothiozole-2-sulfenamide, zinc-2-mercaptotoluimidazole, dithiobis(N-methyl piperazine), dithiobis(N-beta-hydroxy ethyl piperazine) and dithiobis(dibenzyl amine). Other additional sulfur donors, may be, for example, thiuram and morpholine derivatives. Representative of such donors are, for example, but not limited to, dimorpholine disulfide, dimorpholine tetrasulfide, tetramethyl thiuram tetrasulfide, benzothiazyl-2, N-dithiomorpholide, thioplasts, dipentamethylenethiuram hexasulfide, and disulfidecaprolactam.

Accelerators are used to control the time and/or temperature required for vulcanization and to improve the properties of the vulcanizate. In one embodiment, a single accelerator system may be used, i.e., a primary accelerator. Conventionally and preferably, a primary accelerator(s) is used in total amounts ranging from 0.5 to 4 phr, preferably 0.8 to 1.5 phr. Combinations of a primary and a secondary accelerator might be used with the secondary accelerator being used in smaller amounts (of 0.05 to 3 phr) in order to activate and to improve the properties of the vulcanizate. Delayed action accelerators may be used. Vulcanization retarders might also be used. Suitable types of accelerators are amines, disulfides, guanidines, thioureas, thiazoles, thiurams, sulfenamides, dithiocarbamates, and xanthates. Preferably, the primary accelerator is a sulfenamide. If a second accelerator is used, the secondary accelerator is preferably a guanidine, dithiocarbamate, or thiuram compound.

Typical amounts of tackifier resins, if used, comprise 0.5 to 10 phr, usually 1 to 5 phr. Typical amounts of processing aids comprise 1 to 50 phr. Such processing aids include, for example, aromatic, naphthenic, and/or paraffinic processing oils. Typical amounts of antioxidants comprise 1 to 5 phr. Representative antioxidants may be, for example, diphenyl-p-phenylenediamine and others such as those disclosed in the *Vanderbilt Rubber Handbook* (1978), pages 344–46. Typical amounts of antiozonants comprise 1 to 5 phr. Typical amounts of fatty acids, which, if used, can include stearic acid, comprise 0.5 to 3 phr. Typical amounts of zinc oxide comprise 2 to 5 phr. Typical amounts of waxes comprise 1 to 5 phr. Often microcrystalline waxes are used. Typical amounts of peptizers comprise 0.1 to 1 phr. Typical peptizers may be, for example, pentachlorothiophenol and dibenzamidodiphenyl disulfide.

The rubber composition of this invention can be used for various purposes. For example, it can be used for various tire compounds. Such tires can be built, shaped, molded, and cured by various methods which are known and will be readily apparent to those having skill in such art.

All references cited are incorporated herein as they are relevant to the present invention.

The invention may be better understood by reference to the following examples in which the parts and percentages are by weight unless otherwise indicated.

EXAMPLES

Example 1

Preparation of 3-(methyldiacetoxysilyl)-1-propyl thioacetate

A 5-liter flask was fitted with a 15-plate Oldershaw distilling column (28 mm plate diameter), to which was attached a condenser and distilling head capable of providing a controlled and adjustable reflux ratio. Heat was supplied to the flask using an electric heating mantle regulated by a controller coupled to an electronic temperature regulator. The vapor temperature in the head was monitored also. The system was maintained under an atmosphere of nitrogen. Control of the vacuum was enhanced via a bleeder valve inserted between the cold trap and the distillation head.

738.1 grams of 3-(methyldimethoxysilyl)-1-propyl mercaptan and 1892.2 grams of acetic anhydride were added to the 5-liter flask. The mixture was heated with stirring until the first drops of liquid began to collect from the head, at which time the collection rate was adjusted to 1–2 drops per second. Heat was supplied to the flask at a sufficient rate so as to maintain a reflux ratio of no less than 8:1, but not sufficient to cause column flooding. The collection temperature rapidly stabilized to 54° C. The collection rate was increased and adjusted to maintain a collection temperature of not more than 55° C. until a total of 506 grams of a clear, colorless liquid had been collected. The distillate had an odor of methyl acetate and was immiscible with and unresponsive toward aqueous sodium carbonate. Further distillation began with a collection at 54° C., with a gradual tendency toward higher temperatures and slower collection rates until a steady collection in the range of 115° to 120° C. was maintained. 650 grams of a clear, colorless liquid was collected, which had an odor of acetic acid and methyl acetate and demonstrated vigorous effervescence with aqueous sodium carbonate. After cooling, an additional 361 grams of acetic anhydride were added to the contents of the 5-liter flask, and the distillation was reinitiated. Collection eventually stabilized at 140° C., yielding 493 grams of distillate. The temperature in the 5-liter flask had risen to 180° C. whereupon the heating was stopped. Both acetic acid and acetic anhydride could be detected in the distillate by odor. Its response with aqueous sodium carbonate was similar to the previous sample. A final sample of distillate was collected under vacuum. The vacuum was regulated and maintained at the level required to collect the distillate at a temperature near that of the cooling water used to remove heat from the condenser using the bleeder valve. The temperature in the 5-liter flask was limited to 150° C. during this procedure. The bleeder valve gradually was opened. An additional 428 grams of distillate collected. The final distillate had an odor of acetic anhydride. At this point, the temperature in the 5-liter flask was slowly increased, leading to the fractional distillation of the product at <0.7 kPa. An initial 12-gram fraction was collected at <1 drop/second with a reflux ratio of >10:1. A second fraction of 950 grams of a clear, colorless liquid was collected at a substantially faster rate with a reflux ratio of >5:1. The distillation was terminated when the temperature of the 5-liter flask reached 180° C., leaving a dark brown, viscous residue of 170 grams. The second fraction was product of 98.5 percent purity (GC); distilled yield, 83 percent.

Example 2

Preparation of 3-(trimethoxysilyl)-1-propyl thioacetate

The apparatus used was identical to that of Example 1. 1,074 grams of 3-(trimethoxysilyl)-1-propyl mercaptan and 561.4 grams of acetic anhydride were added to the 5-liter flask. The system was evacuated, followed by continuous application of vacuum using the bleeder valve in the nearly shut position. The temperature of the 5-liter flask was increased gradually to 120° C., at which time condensate began collecting at <30° C. The distillation was continued until nothing more collected with the 5-liter flask now at a temperature of 155° C., at which time the heating was stopped, yielding 184 grams of a clear, colorless liquid with a distinct odor of methyl acetate. Its specific gravity of 0.898 combined with a negative response to aqueous sodium carbonate indicated that a substantial portion of methanol was probably present. The temperature of the 5-liter flask was now gradually raised to 195° C., yielding an additional total of 266 grams of condensate. The distillation was continued with gradual heating of the 5-liter flask to 225° C. and with the bleeder valve open. 379 grams of a clear liquid was collected at a maximum head temperature of 104° C. GC analysis indicated that both the starting and product silanes were major components of the distillate, with small amounts of acetic acid detectable by odor.

The contents of the 5-liter flask were emptied into and stored in a 32-oz. (947 ml) bottle under nitrogen. The 5-liter flask was charged with the distillate, which was redistilled with the bleeder valve wide open. A large first fraction contained mostly the starting blocked mercaptosilane. A second, clear and colorless 75 gram fraction was collected at 70° C. This fraction was product of >90 percent purity (GC); distilled yield, 6 percent. The product also contained derivative containing methoxy-Si and acetoxy-Si groups and SiOSi crosslinks.

Example 3

Preparation of 3-(trimethoxysilyl)-1-propyl thioacetate derivative containing acetoxy-Si groups and SiOSi crosslinks This product was the undistilled liquid that remained in the distilling flask of Example 2 after removal of the second, clear and colorless 75 gram fraction, which was collected at 70° C. and was the product of Example 2 of >90 percent purity (GC); distilled yield, 6 percent.

Example 4

Preparation of 3-(trimethoxysilyl)-1-propyl thioacetate derivative containing acetoxy-Si groups and SiOSi crosslinks The apparatus used was identical to that of Example 1. 1,775 grams of 3-(trimethoxysilyl)-1-propyl mercaptan was added to the 5-liter flask. A total of 4,719 grams of acetic anhydride was set aside for reaction with the mercaptosilane, of which 1,002 grams was added to the 5-liter flask along with the mercaptosilane. The heat flow to the 5-liter flask was increased gradually until a steady collection of distillate was established at a head temperature of 54° C. A total of 840 grams of distillate was collected, which was found to contain methyl acetate, acetic acid, and methanol in a 100/2/2.7 molar ratio by NMR analysis. An additional 2,015 grams of acetic anhydride was added to the cooled 5-liter flask, and the distillation resumed, yielding an additional 923 grams of distillate. The procedure was then repeated a third time with a 701 gram addition of acetic anhydride, yielding 834 grams of distillate. The application of vacuum to the head was then begun. The vacuum was regulated and maintained at the level required to collect the distillate at a temperature near that of the cooling water used to remove heat from the condenser via the bleeder valve. The temperature in the 5-liter flask was limited to 170° C. during this procedure. The bleeder valve was opened gradually as the collection rate began to diminish. An additional 896 grams of distillate collected, whereupon any remaining liquids in the column and head evaporated. GC analysis of the final distillate indicated that essentially nothing less volatile than acetic anhydride had distilled over. The contents of the flask cooled to a viscous, dark brown oil, which was stored under nitrogen.

Example 5

Preparation of
3-(propionylthio)-1-propyltrimethoxysilane 816 grams of 3-mercapto-1-propyltrimethoxysilane, 871 grams of 25 weight percent methanolic solution of sodium methoxide, and 1,724 grams of toluene were charged to a 5-liter flask under an atmosphere of nitrogen. The stirred mixture developed a pinkish color. Methanol was removed from the flask by distilling off a methanol-toluene azeotrope, during which time the contents of the flask turned colorless. The appearance of a strong density current in the distillate which coincided with an increased in distillation head temperature from 63° C. to 108° C. signaled the point at which methanol removal from the flask was complete. With continued stirring, the contents of the flask were allowed to cool and were placed in an ice-water bath. 361 grams of propionyl chloride was added to the flask dropwise and/or in small portions with continued stirring in an ice-water bath until the reaction was complete. Aliquots of the stirred mixture were taken periodically and placed onto pH paper. An alkaline reading indicated the completion of the reaction. The final mixture was a white suspension of NaCl in a toluene solution of the product. This mixture was filtered and the solvent was removed from the filtrate to yield a light brown product. Gas chromatography indicated 5 percent 3-mercapto-1-propyltrimethoxysilane, 25 percent of 3-(methylthio)-1-propyltrimethoxysilane, and 70 percent of 3-(acetylthio)-1-propyltrimethoxysilane (product). Flash distillation from one to two grams of powdered sodium methoxide yielded a colorless product. The sodium methoxide was added to ensure that any remaining acidity was neutralized. Further optional fractional distillation yielded a product in excess of 98 percent purity by GC.

Example 6

Preparation of
3-(propionylthio)-1-propyltrimethoxysilane 1,035 grams of 3-mercapto-1-propyltrimethoxysilane, 1,096 grams of a 25 weight percent methanolic solution of sodium methoxide, and 1,764 grams of toluene were charged to a 5-liter flask under an atmosphere of nitrogen. The stirred mixture developed a pinkish color. The flask was placed into a water bath at 64° C. Methanol was removed from the flask by distilling off a methanol-toluene azeotrope under a partial vacuum. The vacuum was kept such that the temperature in the distillation head was maintained at 30° to 35° C. during which time 1,500 ml of distillate, consisting of a toluene-methanol azeotrope, was collected. During this time the contents of the flask turned colorless. An additional 429 grams of toluene were added, and the distillation resumed. The appearance of a strong density current in the distillate, which coincided with an increase in distillation head temperature from 35° to 55° C., and the appearance of a changing liquid surface tension in the condenser signaled the point at which methanol removal from the flask was complete. The contents of the flask had become a viscous fluid. With continued stirring, the contents of the flask were allowed to cool. The flask was placed in an ice-water bath, resulting in what appeared to be a thick paste. 427 grams of propionyl chloride was added to the flask dropwise and/or in small portions with continued stirring in an ice-water bath until the reaction was complete. Aliquots of the stirred mixture were taken periodically. An alkaline reading indicated the completion of the reaction. The final mixture was a white suspension of NaCl in a toluene solution of the product. This mixture was filtered, and the solvent was removed from the filtrate to yield a nearly colorless product. Gas chromatography indicated (by weight) 3 percent of 3-mercapto-1-propyltrimethoxysilane, 1 percent of 3-(methylthio)-1-propyltrimethoxysilane, and 96 percent of 3-(acetylthio)-1-propyltrimethoxysilane (product). Flash distillation from one to two grams of powdered sodium methoxide yielded a colorless product. The sodium methoxide was added to ensure that any remaining acidity was neutralized. Further optional fractional distillation yielded a product in excess of 98 percent purity by GC.

Example 7

Preparation of
3-(benzoylthio)-1-propyltriethoxysilane 763 grams of 3-mercapto-1-propyltriethoxysilane and 1,013 grams of a 21 weight percent ethanolic solution of sodium ethoxide were charged to a 5-liter flask under an atmosphere of nitrogen. 850 grams of ethanol was distilled from this mixture at a maximum temperature of 45° C. at 48 kPa. 1,550 grams of toluene was added to the contents of the flask under nitrogen. The remaining ethanol was removed from the flask by distilling off an ethanol-toluene azeotrope under a maximum absolute pressure of 48 kPa at a maximum temperature of 60° C. The vacuum was kept such that the temperature in the distillation head was maintained at 30° to 40° C. The appearance of a strong density current in the distillate which coincided with an increase in distillation head temperature from 35° to about 60° C. and the appearance of a changing liquid surface tension in the condenser signaled the point at which ethanol removal from the flask was complete. At the end of this procedure the contents of the flask had become a clear, orange liquid.

With continued stirring, the contents of the flask were allowed to cool to ambient temperature. 418 grams of benzoyl chloride was added to the flask dropwise and/or in small portions at a sufficiently slow rate to prevent the temperature from rising above 50° C. At the completion of the benzoyl chloride addition, stirring was continued for an additional day. The stirring was initially sufficiently vigorous to break up any chunks and inhomogeneities in the mixture. The resulting final mixture was a white suspension of NaCl in a toluene solution of the product. This mixture was filtered, and the solvent was removed from the filtrate to yield a light yellow-brown product which gave an acidic response to pH paper. Sufficient powdered sodium ethoxide was stirred into the product to neutralize all of the acidity. Flash distillation at <0.7 kPa yielded a light pink product containing about 10 percent by gas chromatography each of ethyl benzoate and 1-sila-2-thia-1,1-diethoxycyclopentane, which formed because of base catalyzed decomposition during the distillation. A second flash distillation was performed in which the first 30 percent of the product was removed as a forecut. No base or acid was present. The second fraction was a product of light pink color in excess of 98 percent purity by GC.

Example 8

Preparation of 2-(acetylthio)-1-ethyltriethoxysilane 2,513 grams of vinyltriethoxysilane was added to a 5-liter flask and brought to reflux with stirring. A 25 ml forecut was distilled off to remove volatile impurities. The heating was stopped, and a first, 335 gram, portion of a total of two portions of 1,005 grams of thiolacetic acid was added over a period of several minutes at a rate to maintain a smooth reflux. Heat was supplied toward the end of the addition, as necessary, to maintain the reflux. 0.8 gram of di-t-butyl peroxide was added down the condensers, resulting in an immediate reaction as evidenced by a reflux rate acceleration. Power to the heating mantle was cut. During the reflux, the temperature rose to near 160° C. within several minutes, whereupon the reflux subsided and the light yellow contents of the pot began to cool.

When the contents of the pot had reached 150° C., an additional 670 grams of thiolacetic acid was added in a manner similar to the first addition. 20 ml. of forecut were collected, and 1.6 grams of di-t-butyl peroxide was again added. A slight increase in reflux rate was observed within several minutes. After 10 to 15 minutes, the pot reached a maximum temperature of 155° C. and subsequently began to cool. At 150° C. the temperature was maintained by the heating mantle for one hour. The pot was allowed to cool under nitrogen. Gas chromatography analysis indicated (by weight) 2 percent thiolacetic acid, 16 percent vinyltriethoxysilane, 5 percent 1-(acetylthio)-1-ethyltriethoxysilane (alpha adduct), 68 percent 2-(acetylthio)-1-ethyltriethoxysilane (beta adduct product), and 9 percent balance (mainly heavies).

Example 9

Preparation of 3-(octanoylthio)-1-propyltriethoxysilane

Into a 12-liter, three-necked round bottom flask equipped with mechanical stirrer, addition funnel, thermocouple, heating mantle, $N_2$ inlet, and temperature controller were charged 1,021 grams of 3-mercaptopropyltriethoxysilane (SILQUEST® A-1891 silane from OSi Specialties, Inc., a subsidiary of Crompton Corp. of Greenwich, Connecticut), 433 grams of triethylamine, and 3,000 ml hexane. The solution was cooled in an ice bath, and 693 grams of octanoyl chloride were added over a two hour period via the addition funnel. After addition of the acid chloride was complete, the mixture was filtered two times, first through a 0.1 µm filter and then through a 0.01 µm filter, using a pressure filter, to remove the salt. The solvent was removed under vacuum. The remaining yellow liquid was vacuum distilled to yield 1,349 grams of octanoylthiopropyltriethoxysilane as a clear, very light yellow liquid. The yield was 87 percent.

Example 10

Preparation of 3-(acetylthio)-1-propyltriethoxysilane

This example illustrates the preparation of a thiocarboxylate alkoxysilane from a salt of a thiolcarboxylic acid using as a solvent the alcohol corresponding to the silane alkoxy group. Into a 250 ml, three-neck round bottomed flask equipped with magnetic stir bar, temperature probe/controller, heating mantle, addition funnel, condenser, and $N_2$ inlet was charged 63 grams of a 21 weight percent sodium ethoxide in ethanol. Fifteen grams of thiolacetic acid was added slowly, keeping the temperature below 65° C. The solution was allowed to cool to room temperature, and 48 grams of chloropropyltriethoxysilane was added via the addition funnel. After addition was complete, the solution was heated to 70° C. for 24 hours whereupon a white solid formed. Analysis of the solution by gas chromatography showed a 78 percent yield of acetylthiopropyltriethoxysilane.

Example 11

Preparation of Acetylthiomethyltriethoxysilane

This example illustrates the preparation of a thiocarboxylate alkoxysilane from a salt of a thiolcarboxylic acid using a nonprotic solvent. 88 grams of powdered sodium ethoxide and 600 ml diglyme were charged into a one-liter, three-neck round bottomed flask equipped with magnetic stir bar, temperature probe/controller, heating mantle, addition funnel, condenser, $N_2$ inlet, and ice water bath. The solution was cooled to 8° C., and 105 grams of thiolacetic acid was added slowly via the addition funnel, keeping the temperature below 60° C. The solution was allowed to cool to 35° C., and 250 grams of chloromethyltriethoxysilane was added via the addition funnel. After addition was complete, the solution was heated to 70° C., where a brief exotherm to 120° C. was observed. The solution was heated at 70° C. for an additional three hours. A white solid formed which was filtered first through a 0.1 µm pressure filter and then a 0.01 µm filter to give a clear, black solution. The solvent was removed under reduced pressure, and the remaining liquid vacuum distilled to yield 163 grams of a clear and colorless liquid, a 55 percent yield.

Example 12

The Use of Silanes of Examples 1 to 4 in Low Rolling Resistant Tire Tread Formulation A model low rolling resistance passenger tire tread formulation as described in Table 1 and a mix procedure were used to evaluate representative examples of the silanes of the present invention. The silane in Example 1 was mixed as follows in a "B" BANBURY® (Farrell Corp.) mixer with a 103 cu. in. (1690 cc) chamber volume. The mixing of the rubber masterbatch was done in two steps. The mixer was turned on with the mixer at 120 rpm and the cooling water on full. The rubber polymers were added to the mixer and ram down mixed for 30 seconds. Half of the silica and all of the silane with approximately 35–40 grams of this portion of silica in an ethylvinyl acetate (EVA) bag were added and ran down mixed for 30 seconds. The remaining silica and the oil in an EVA bag were next added and ram down mixed for 30 seconds. The mixer throat was thrice dusted down, and the mixture ram down mixed for 15 seconds each time. The mixer's mixing speed was increased to 160 or 240 rpm, as required to raise the temperature of the rubber masterbatch to between 160° and 165° C. in approximately one minute. The masterbatch was dumped (removed from the mixer), a sheet was formed on a roll mill set at about 50° to 60° C., and then allowed to cool to ambient temperature.

The rubber masterbatch was added to the mixer with the mixer at 120 rpm and cooling water turned on full and ram down mixed for 30 seconds. The remainder of the ingredients was added and ram down mixed for 30 seconds. The mixer throat was dusted down, the mixer speed increased to 160 or 240 rpm so that the contents reached a temperature between 160° and 165° C. in approximately two minutes. The rubber masterbatch was mixed for eight minutes, and the speed of the BANBURY mixer as adjusted to maintain the temperature between 160° and 165° C. The masterbatch was dumped (removed from the mixer), a sheet was formed on a roll mill set at about 50° to 60° C., and then allowed to cool to ambient temperature.

The rubber masterbatch and the curatives were mixed on a 6 in.×13 in. (15 cm×33 cm) two roll mill that was heated to between 50° and 60° C. The sulfur and accelerators were added to the rubber masterbatch and thoroughly mixed on the roll mill and allowed to form a sheet. The sheet was cooled to ambient conditions for 24 hours before it was cured. The Theological properties were measured on a Monsanto R-100 Oscillating Disk Rheometer and a Monsanto M1400 Mooney Viscometer. The specimens for measuring the mechanical properties were cut from 6 mm plaques cured for 35 minutes at 160° C. or from 2 mm plaques cured for 25 minutes at 160° C.

Silanes from Examples 2 to 4 were compounded into the tire tread formulation according to the above procedure. The performance of the silanes prepared in Examples 1 to 4 was compared to the performance of no silane coupling agent (Silane α), two silanes, one of which is practiced in the prior art, bis-(3-triethoxysilyl-1-propyl)tetrasulfide (TESPT, Silane β), the other 3-triethoxysilyl-1-propylmercaptan (TESPM, Silane γ) which is the product resulting from the loss of a carboxyl blocking group from a representative example of the silanes of the present invention. The results of this procedure are tabulated below in Table 2.

TABLE 1

Model Low Rolling Resistance Tread Formulation

| PHR | Ingredient |
|---|---|
| 75 | sSBR (12% styrene, 46% vinyl, $T_g$: 42° C.) |
| 25 | BR (98% cis, $T_g$: 104° C.) |
| 80 | Silica (150–190 $m^2$/gm, ZEOSIL 1165MP, Rhone-Poulenc) |
| 32.5 | Aromatic process oil (high viscosity, Sundex 8125, Sun) |
| 2.5 | Zinc oxide (KADOX 720C, Zinc Corp.) |
| 1 | Stearic acid (INDUSTRENE, Crompton) |
| 2 | 6PPD antiozonant (SANTOFLEX 6PPD, Flexsys) |
| 1.5 | Microcrystalline wax (M-4067, Schumann) |
| 3 | N330 carbon black (Engineered Carbons) |
| 1.4 | Sulfur (#104, Sunbelt) |
| 1.7 | CBS accelerator (SANTOCURE, Flexsys) |
| 2 | DPG accelerator (PERKACIT DPG-C, Flexsys) |

The following tests were conducted with the following methods (in all examples):

Mooney Scorch @ 135° C. (ASTM Procedure D1646); Mooney Viscosity @ 100° C. (ASTM Procedure D1646); Oscillating Disc Rheometer (ODR) @ 149° C., 1° arc, (ASTM Procedure D2084); Physical Properties, cured t90 @ 149° C. (ASTM Procedures D412 and D224) (G' and G" in dynes/$cm^2$); DIN Abrasion, $mm^3$ (DIN Procedure 53516); and Heat Build (ASTM Procedure D623).

TABLE 2

Performance of Representative Silanes in a Model Low Rolling Resistance Passenger Tire Tread Formulation

| Silane | α | β | Ex.4 | Ex.3 | Ex.1 | Ex.2 | γ | γ |
|---|---|---|---|---|---|---|---|---|
| Amount | — | 7.4 | 7.4 | 7.4 | 7.4 | 8.3 | 3.8 | 6.35 |
| Mooney Viscosity at 100° C. | | | | | | | | |
| ML1 + 4 | 130 | 67 | 65 | 58 | 73 | 63 | 74 | 121 |
| Mooney Scorch at 135° C. | | | | | | | | |
| MS1+, $t_3$, minutes | 9.5 | 6.7 | 4.3 | 6.3 | 2.2 | 6.3 | 6.3 | 2.8 |
| MS1+, $t_{18}$, | 11.0 | 10.1 | 5.9 | 7.8 | 3.2 | 7.7 | 8.4 | 3.7 |
| ODR @ 149° C., 1° arc, 30 minute timer | | | | | | | | |
| $M_L$, dN-M | 26.9 | 8.5 | 8.5 | 7.2 | 9.3 | 7.8 | 11.5 | 14.8 |
| $M_H$, dN-M | 44.5 | 30.8 | 31.0 | 31.4 | 34.8 | 30.5 | 27.8 | 33.9 |
| $t_s$1, minutes | 5.4 | 4.8 | 2.5 | 3.8 | 1.6 | 3.8 | 3.8 | 2.0 |
| t90, minutes | 10.5 | 17.8 | 8.0 | 8.0 | 8.1 | 7.5 | 15.3 | 15.0 |
| Physical Properties, cured t90 @ 149° C. | | | | | | | | |
| Hardness, Shore A | 66 | 57 | 59 | 60 | 62 | 60 | 52 | scorched |
| Elongation, % | 900 | 400 | 540 | 520 | 490 | 450 | 360 | |
| 100% Mod., kg/$cm^2$ | 10.5 | 19.0 | 19.0 | 18.3 | 22.5 | 23.2 | 15.5 | not |
| 200% Mod., kg/$cm^2$ | 15.5 | 56.9 | 49.2 | 46.4 | 59.8 | 66.1 | 45.0 | cured |
| 300% Mod., kg/$cm^2$ | 24.6 | 128.0 | 101.2 | 96.2 | 116.0 | 129.4 | 104.8 | |
| Tensile, kg/$cm^2$ | 137.1 | 208.1 | 234.8 | 218.0 | 237.6 | 222.9 | 139.2 | |
| Dynamic Properties @ 0.15% | | | | | | | | |

TABLE 2-continued

Performance of Representative Silanes in a Model Low Rolling Resistance Passenger Tire Tread Formulation

| Silane | α | β | Ex.4 | Ex.3 | Ex.1 | Ex.2 | γ | γ |
|---|---|---|---|---|---|---|---|---|
| strain, 10 Hz, torsion mode (2nd sweep) | | | | | | | | |
| G' @ 0° C., × $10^7$ | 26.8 | 5.92 | 9.22 | 9.42 | 1.26 | 6.41 | 3.17 | |
| G' @ 60° C., × $10^7$ | 12.7 | 2.76 | 4.26 | 3.89 | 5.36 | 3.02 | 1.75 | |
| G" @ 0° C., × $10^7$ | 2.87 | 1.26 | 1.81 | 1.84 | 2.14 | 1.3 | 5.69 | |
| G" @ 60° C., × $10^6$ | 11.2 | 2.48 | 4.00 | 3.85 | 4.94 | 2.71 | 2.13 | |
| Tan delta @ 0° C. | 0.1070 | 0.2124 | 0.1968 | 0.1952 | 0.169 | 0.202 | 0.202 | |
| Tan delta @ 60° C. | 0.0876 | 0.09 | 0.0939 | 0.0988 | 0.092 | 0.089 | 0.121 | |
| Ratio 0° C./60° C. | 1.22 | 2.36 | 2.10 | 1.98 | 1.84 | 2.25 | 1.67 | |
| Heat Building-up, 100° C. ambient, 18.5% compression, 143 psi (99 kPa) load, 25 minutes | | | | | | | | |
| Delta T, ° C. | 66 | 13 | 22 | 19 | 18 | 17 | | |
| Set, % | *** | 6.3 | 10.9 | 8.8 | 8.0 | 6.9 | | |

*** delaminated in 9

Example 13

The Use of Silane of Example 1 in Low Rolling Resistance Tire Formulation Activated by Varying Levels of DPG The model low rolling resistance passenger tire tread formulation and mixing procedure of Example 11 were used to evaluate the silane of Example 1 at three levels of N,N-diphenylguanidine (DPG). The results are tabulated below in Table 3.

TABLE 3

The Effect of DPG on the Compounding and Curing of a Model Low Rolling Resistance Passenger Tire Tread Formulation

| Run | A | B | C |
|---|---|---|---|
| phr DPG | 2.00 | 0.5 | 1.25 |
| Mooney viscosity @ 100° C. | | | |
| ML 1 + 4 | 75 | — | — |
| Mooney scorch @ 135° C. | | | |
| $M_V$ | 41 | — | — |
| MS 1+, $t_3$, minutes | 2.5 | 15.3 | 6.2 |
| MS 1+, $t_{18}$, minutes | 3.6 | 24.1 | 8.3 |
| ODR @ 149° C., 1° arc, 30 minute timer | | | |
| $M_L$, dN-M | 9.8 | 9.4 | 8.6 |
| $M_H$, dN-M | 35.7 | 28.8 | 33.4 |
| $t_s1$, minutes | 1.8 | 8.0 | 3.4 |
| t90, minutes | 8.0 | 22.5 | 11.8 |
| Physical properties, cured t90 @ 149° C. | | | |
| Hardness, Shore A | 63 | 59 | 62 |
| Elongation, % | 550 | 620 | 560 |
| 100% Modulus, kg/cm² | 21.1 | 19.0 | 22.5 |
| 200% Modulus, kg/cm² | 55.5 | 42.9 | 55.5 |
| 300% Modulus, kg/cm² | 106.9 | 80.9 | 106.2 |
| Tensile, kg/cm² | 236 | 209.5 | 234.1 |
| DIN Abrasion, mm³ | 85 | 69 | 72 |
| Dynamic properties @ 10 Hz, 0.15 strain, torsion mode | | | |
| G' @ 0° C., × $10^7$ | 14.8 | 14.1 | 12.6 |
| G' @ 60° C., × $10^7$ | 6.23 | 5.97 | 5.64 |
| G" @ 0° C., × $10^7$ | 23.0 | 26.4 | 22.1 |
| G" @ 60° C., × $10^6$ | 6.55 | 7.30 | 6.01 |
| Tan delta @ 0° C. | 0.1551 | 0.1872 | 0.1753 |
| Tan delta @ 60° C. | 0.1053 | 0.1189 | 0.1035 |
| Ratio 0° C./60° C. | 1.47 | 1.57 | 1.69 |

Example 14

Shoe Sole Compound Compositions

Formulation: 60 Budene 1207 BR, 40 SMR5L NR, 45 ZEOSIL 1165MP Silica, 5 CALSOL 5550 Process Oil, 3 CARBOWAX 3350 PEG, 5 KADOX 720C Zinc Oxide, 1 INDUSTRENE R Stearic Acid, 1 BHT Antioxidant, 1 SUNOLITE 240 Wax, 1.9 Rubbermakers Sulfur 104, 1.3 MBTS, 0.5 MBT, 0.2 TMTM, Silane—SILQUEST A-1289 silane (TESPT) or acetylthiopropyltriethoxysilane (Acetyl). The amounts of each are in phr. The term "Add Sulfur" or "Add S" means that additional sulfur was added to make the amount of sulfur in the Acetyl equivalent to the amount of sulfur delivered by TESPT. The results are set forth in Table 4 below.

TABLE 4

| Silane | None | TESPT | TESPT | Acetyl | Acetyl | Acetyl | Acetyl |
|---|---|---|---|---|---|---|---|
| Add Sulfur | — | — | — | — | X | — | X |
| Amount, phr | — | 2 | 4 | 2 | 2 | 4 | 4 |
| Mooney Scorch at 135° C. | | | | | | | |
| MV | 51 | 42 | 40 | 36 | | 33 | |
| MS1+, $t_3$, minutes | 5.0 | 4.3 | 4.3 | 6.9 | | 7.4 | |
| MS1+, $t_{18}$, minutes | 5.8 | 5.3 | 5.3 | 8.2 | | 8.8 | |
| Mooney Viscosity @ 100° C. | | | | | | | |
| ML1 + 4 | 96 | 78 | 76 | 74 | | 71 | |
| ODR @ 149° C., 1° arc, 12 minute timer | | | | | | | |
| $M_L$, dN-M | 19.7 | 14.9 | 14.0 | 12.2 | 11.5 | 10.4 | 10.2 |
| $M_H$, dN-M | 59.7 | 57.4 | 54.2 | 52.0 | 52.8 | 49.3 | 49.8 |
| $t_s1$, minutes | 3.5 | 2.8 | 2.8 | 4.3 | 3.8 | 4.7 | 4.4 |
| t90, minutes | 5.7 | 5.6 | 5.9 | 7.5 | 7.1 | 8.2 | 8.2 |
| Physical Properties, cured t90 @ 149° C. | | | | | | | |
| Hardness, Shore A | 67 | 67 | 66 | 66 | 66 | 66 | 66 |
| Elongation, % | 630 | 570 | 570 | 540 | 440 | 500 | 460 |
| 100% Mod., kg/cm$^2$ | 19.7 | 23.9 | 25.3 | 26.7 | 26.7 | 26.7 | 27.4 |
| 200% Mod., kg/cm$^2$ | 36.6 | 50.6 | 54.1 | 56.2 | 59.1 | 55.5 | 59.8 |
| 300% Mod., kg/cm$^2$ | 58.3 | 86.5 | 91.4 | 97.7 | 103.3 | 96.3 | 105.5 |
| Tensile, kg/cm$^2$ | 187.0 | 204.6 | 222.2 | 201.1 | 174.4 | 189,8 | 189.1 |
| DIN Abrasion, mm$^3$ | 86 | 75 | 67 | 74 | 71 | 65 | 73 |
| Akron Abrasion, mm$^3$ | 0.46 | 0.48 | 0.35 | 0.39 | 0.41 | 0.45 | 0.44 |

Example 15

Low Rolling Resistance Tire Formulations

The following silanes were tested in low rolling resistance tire formulations; TESPT (A); TESPM (B); 3-acetylthio-1-propyltrimethoxysilane (C), 3-acetylthio-1-propyltriethoxysilane (D), 3-octanoylthio-1-propyltriethoxysilane (E); 3-palmitoylthio-1-propyltriethoxysilane (F); 3-ethylhexanoyl-1-propyltriethoxysilane (G); 3-propionylthio-1-propyltrimethoxysilane (H); 3-benzoylthio-1-propyltriethoxysilane (I); acetylthiomethyltriethoxysilane (J), acetylthioethyltrimethoxysilane (K), acetylthioethyltriethoxysilane (L), acetothioethylmethyldimethoxysilane (M), acetylthiooctyltrimethoxysilane (N), acetylthiooctyltriethoxysilane (O), acetylthiocyclohexylethyltrimethoxysilane (P), and acetothionorbornylethyltrimethoxysilane (Q). The formulation was (amounts in phr) 75 SOLFLEX 1216 sSBR, 25 Budene 1207 BR, 80 ZEOSIL 1165MP silica, 32.5 SUNDEX 3125 process oil, 2.5 KADOX 720C zinc oxide, 1.0 INDUSTRENE R stearic acid, 2.0 SANTOFLEX 13 antiozonant, 1.5 M4067 microwax, 3.0 N330 carbon black, 1.4 Rubbermakers sulfur 104, 1.7 CBS, 2.0 DPG, Silane as shown.

TABLE 5

| Silane | A | B | B | C | C | D | D |
|---|---|---|---|---|---|---|---|
| Add S | | | X | | X | | X |
| Amount, phr | 7.0 | 6.36 | 6.36 | 6.33 | 6.33 | 7.45 | 7.45 |
| Mooney Viscosity at 100° C. | | | | | | | |
| ML1 + 4 | 94 | 74 | 74 | 72 | — | 62 | — |
| Mooney Scorch at 135° C. | | | | | | | |
| MS1+, $t_3$, minutes | 6.2 | 9.9 | 9.0 | 6.9 | 7.5 | 6.3 | 6.3 |
| MS1+, $t_{18}$, minutes | 8.9 | 12.6 | 11.5 | 9.3 | 10.2 | 7.6 | 7.8 |
| ODR @ 149° C., 1° arc, 30 minute timer | | | | | | | |
| $M_L$, dN-M | 9.6 | 8.1 | 8.1 | 8.7 | 8.5 | 7.9 | 7.7 |
| $M_H$, dN-M | 31.8 | 29.5 | 34.5 | 32.0 | 36.7 | 29.9 | 33.9 |
| $t_s1$, minutes | 4.5 | 5.4 | 5.1 | 4.1 | 4.5 | 3.6 | 3.5 |
| t90, minutes | 17.6 | 10.4 | 14.1 | 11 | 11.5 | 8.0 | 7.5 |
| Physical Properties, cured t90 @ 149° C. | | | | | | | |
| Hardness, Shore A | 57 | 58 | 60 | 64 | 66 | 59 | 60 |
| Elongation, % | 420 | 560 | 440 | 660 | 570 | 630 | 540 |
| 100% Mod., kg/cm$^2$ | 20.4 | 16.9 | 22.5 | 17.6 | 22.5 | 15.5 | 19.0 |
| 200% Mod., kg/cm$^2$ | 58.4 | 40.1 | 59.8 | 38.7 | 54.8 | 34.5 | 49.9 |

TABLE 5-continued

| | | | | | | | |
|---|---|---|---|---|---|---|---|
| 300% Mod., kg/cm² | 123.7 | 84.4 | 123.0 | 73.8 | 105.5 | 71.7 | 104.1 |
| Tensile, kg/cm² | 210.9 | 210.3 | 211.6 | 225.0 | 250.3 | 223.6 | 236.2 |
| DIN Abrasion mm³ | 71 | 69 | 76 | 114 | 97 | 131 | 90 |
| Heat Build-up @ 100° C., 17.5% compression, 99 kPa static, 25 minute run | | | | | | | |
| Delta T, ° C. | 13.3 | 18.9 | 13.3 | 32.2 | 18.3 | 21.1 | 13.3 |
| Permanent set, % | 6.2 | 10.5 | 6.3 | 25.3 | 12.3 | 14.5 | 9.8 |
| Dynamic Properties @ 0.15% strain, 10 Hz, torsion mode | | | | | | | |
| G' @ 0° C., dyn/cm² × 10⁷ | 6.73 | 12.8 | 12.4 | 20.1 | 16.6 | 12.8 | 10.4 |
| G' @ 60° C., dyn/cm² × 10⁷ | 3.00 | 5.13 | 5.15 | 8.73 | 2.67 | 5.10 | 1.93 |
| G" @ 0° C., dyn/cm² × 10⁷ | 1.46 | 2.44 | 2.43 | 3.39 | 7.06 | 2.47 | 4.05 |
| G" @ 60° C., dyn/cm² × 10⁶ | 2.93 | 5.23 | 4.47 | 8.35 | 5.33 | 5.79 | 3.21 |
| Tan delta @ 0° C. | 0.216 | 0.191 | 0.196 | 0.168 | 0.161 | 0.192 | 0.185 |
| Tan delta @ 60° C. | 0.098 | 0.102 | 0.087 | 0.096 | 0.075 | 0.114 | 0.079 |
| Ratio 0° C./60° C. | 2.22 | 1.88 | 2.26 | 1.75 | 2.15 | 1.68 | 2.34 |

| Silane | E | E | F | F | G | H | H |
|---|---|---|---|---|---|---|---|
| Add S | | X | | X | | | X |
| Amount, phr | | 9.69 | 12.67 | 12.67 | 9.62 | 6.7 | 6.7 |
| Mooney Viscosity at 100° C. | | | | | | | |
| ML1 + 4 | 55 | — | 50 | — | 52 | 66 | — |
| Mooney Scorch at 135+ C. | | | | | | | |
| MS1+, t₃, minutes | 10.4 | 9.6 | 13.0 | 11.9 | 16.8 | 8.3 | 7.7 |
| MS1+, t₁₈, | 11.7 | 11.7 | 14.6 | 13.9 | 19.0 | 9.9 | 9.6 |
| ODR @ 149° C., 1° arc, 30 minute timer | | | | | | | |
| $M_L$, dN-M | 6.7 | 6.8 | 5.7 | 5.7 | 5.5 | 8.2 | 7.9 |
| $M_H$, dN-M | 27.8 | 32.3 | 26.8 | 30.7 | 31.6 | 30.1 | 34.6 |
| $t_s$1, minutes | 5.6 | 5.5 | 7.0 | 6.8 | 9.1 | 4.5 | 4.4 |
| t90, minutes | 11.3 | 9.8 | 12.3 | 11.0 | 14.1 | 9.5 | 9.0 |
| Physical Properties, cured t90 @ 149° C. | | | | | | | |
| Hardness, Shore A | 53 | 55 | 51 | 54 | 56 | 58 | 60 |
| Elongation, % | 600 | 490 | 740 | 610 | 600 | 610 | 540 |
| 100% Mod., kg/cm² | 14.1 | 17.6 | 12.7 | 15.5 | 15.5 | 16,2 | 20.4 |
| 200% Mod., kg/cm² | 34.5 | 49.2 | 27.4 | 36.6 | 35.9 | 38.0 | 52.7 |
| 300% Mod., kg/cm² | 77.3 | 105.5 | 55.5 | 71.0 | 69.6 | 80.2 | 108,3 |
| Tensile, kg/cm² | 227.8 | 213.7 | 205.3 | 186.3 | 175.8 | 234.1 | 244.7 |
| DIN Abrasion mm³ | 99 | 92 | — | — | 157 | 127 | 94 |
| Heat Build-up @ 100° C., 17.5% compression, 99 kPa static, 25 minute run | | | | | | | |
| Delta T, ° C. | 12.2 | 8.9 | — | — | 10.5 | 18.9 | 12.21 |
| Permanent set, % | 5.0 | 4.6 | — | — | 7.0 | 11.0 | 7.7 |
| Dynamic Properties @ 0.15% strain, 10 Hz, torsion mode | | | | | | | |
| G' @ 0° C., dyn/cm² × 10⁷ | 4.80 | 4.62 | 6.40 | 5.93 | 9.29 | 10.1 | 9.54 |
| G' @ 60° C., dyn/cm² × 10⁷ | 2.44 | 0.82 | 2.42 | 1.13 | 1.88 | 4.18 | 1.76 |
| G" @ 0° C., dyn/cm² × 10⁶ | 0.98 | 2.00 | 1.27 | 2.17 | 3.64 | 2.07 | 3.72 |
| G" @ 60° C., dyn/cm² × 10⁶ | 2.14 | 1.27 | 2.34 | 1.23 | 3.08 | 4.62 | 2.72 |
| Tan delta @ 0° C. | 0.205 | 0.177 | 0.199 | 0.191 | 0.202 | 0.205 | 0.184 |
| Tan delta @ 60° C. | 0.088 | 0,064 | 0.097 | 0.057 | 0.085 | 0.110 | 0.073 |
| Ratio 0° C./60° C. | 2.33 | 2.77 | 2.05 | 3.35 | 2.39 | 1.86 | 2.52 |

| Silane | I | J | K | K | L | L | M | M |
|---|---|---|---|---|---|---|---|---|
| Add S | | | | X | | X | | X |
| Amount, phr | 9.1 | 6.7 | 5.96 | 5.96 | 7.08 | 7.08 | 5.54 | 5.54 |
| Mooney Viscosity at 100° C. | | | | | | | | |
| ML1 + 4 | 55 | 69 | 73 | — | 63 | — | 71 | — |
| Mooney Scorch at 135° C. | | | | | | | | |
| MS1+, t₃, minutes | 11.5 | 2.5 | 4.6 | 4.3 | 4.5 | 4.6 | 4.7 | 4.9 |
| MS1+, t₁₈, | 13.5 | 3.5 | 5.6 | 5.6 | 5.3 | 5.6 | 5.8 | 6.1 |

TABLE 5-continued

ODR @ 149° C., 1° arc, 30 minute timer

| | | | | | | | |
|---|---|---|---|---|---|---|---|
| $M_L$, dN-M | 6.2 | 8.8 | 9.5 | 9.0 | 6.8 | 7.7 | 9.4 | 9.3 |
| $M_H$, dN-M | 35.0 | 32.5 | 29.8 | 34.1 | 27.5 | 31.3 | 33.9 | 38.1 |
| $t_s1$, minutes | 6.3 | 1.9 | 2.8 | 2.8 | 2.8 | 2.8 | 3.0 | 2.9 |
| t90, minutes | 11.3 | 17.0 | 16.8 | 15.3 | 11.3 | 9.5 | 13.5 | 11.8 |

Physical Properties, cured t90 @ 149° C.

| | | | | | | | |
|---|---|---|---|---|---|---|---|
| Hardness, Shore A | 62 | 61 | 61 | 65 | 56 | 58 | 66 | 65 |
| Elongation, % | 560 | 440 | 500 | 470 | 580 | 560 | 530 | 530 |
| 100% Mod., kg/cm² | 19.0 | 19.0 | 19.0 | 20.4 | 14.8 | 17.6 | 21.2 | 22.5 |
| 200% Mod., kg/cm² | 47.8 | 51.3 | 43.6 | 51.3 | 33.7 | 42.9 | 47.1 | 55.5 |
| 300% Mod., kg/cm² | 107.5 | 109.0 | 84.4 | 105.5 | 69.6 | 91.4 | 87.9 | 105.5 |
| Tensile, kg/cm² | 210.9 | 198.2 | 184.9 | 208.1 | 199.0 | 234.8 | 196.9 | 225.7 |

| Silane | I | J | K | K | L | L | M |
|---|---|---|---|---|---|---|---|
| DIN Abrasion mm³ | 133 | 88 | 113 | 103 | 133 | 96 | 101 |

Heat Build-up @ 100° C., 17.5% compression, 99 kPa static, 25 minute run

| | | | | | | | |
|---|---|---|---|---|---|---|---|
| Delta T, ° C. | 12.8 | 15.6 | 21.7 | 16.1 | 28.9 | 16.7 | 25.0 |
| Permanent set, % | 7.9 | 10.8 | 13.7 | 8.7 | 23.2 | 11.2 | 17.3 |

Dynamic Properties @ 0.15% strain, 10 Hz, torsion mode

| | | | | | | | |
|---|---|---|---|---|---|---|---|
| G' @ 0° C., dyn/cm² × 10⁷ | 17.9 | 10.8 | 18.2 | 16.1 | 10.1 | 8.94 | 27.7 |
| G' @ 60° C., dyn/cm² × 10⁷ | 2.99 | 2.16 | 6.60 | 2.70 | 4.30 | 1.73 | 9.54 |
| G" @ 0° C., dyn/cm² × 10⁷ | 6.38 | 3.92 | 3.27 | 5.86 | 2.12 | 3.65 | 4.33 |
| G" @ 60° C., dyn/cm² × 10⁶ | 6.83 | 4.87 | 9.41 | 5.92 | 2.92 | 14.0 |
| Tan delta @ 0° C. | 0.167 | 0.201 | 0.180 | 0.167 | 0.210 | 0.193 | 0.156 |
| Tan delta @ 60° C. | 0.107 | 0.124 | 0.143 | 0.101 | 0.124 | 0.080 | 0.147 |
| Ratio 0° C./60° C. | 1.56 | 1.67 | 1.26 | 1.65 | 1.69 | 2.41 | 1.06 |

| Silane | M | N | N | O | O | P | Q |
|---|---|---|---|---|---|---|---|
| DIN Abrasion mm³ | 96 | 100 | 94 | 113 | 97 | 141 | 132 |

Heat Build-up @ 100° C., 17.5% compression, 99 kPa static, 25 minute run

| | | | | | | | |
|---|---|---|---|---|---|---|---|
| Delta T, ° C. | 16.7 | 21.1 | 15.6 | 14.4 | 10.0 | 17.2 | 15.0 |
| Permanent set, % | 9.2 | 16.8 | 12.6 | 11.0 | 7.5 | 12.7 | 10.8 |

Dynamic Properties @ 0.15% strain, 10 Hz, torsion mode

| | | | | | | | |
|---|---|---|---|---|---|---|---|
| G' @ 0° C., dyn/cm² × 10⁷ | 22.2 | 14.9 | 12.4 | 10.2 | 8.10 | 27.6 | 23.8 |
| G' @ 60° C., dyn/cm² × 10⁷ | 3.39 | 5.72 | 2.33 | 4.25 | 1.55 | 3.72 | 3.59 |
| G" @ 0° C., dyn/cm² × 10⁷ | 7.79 | 2.93 | 4.85 | 2.06 | 2.80 | 10.8 | 9.04 |
| G" @ 60° C., dyn/cm² × 10⁶ | 9.17 | 5.75 | 3.62 | 4.06 | 2.44 | 12.4 | 9.61 |
| Tan delta @ 0° C. | 0.153 | 0.197 | 0.187 | 0.202 | 0.192 | 0.135 | 0.151 |
| Tan delta @ 60° C. | 0.118 | 0.101 | 0.075 | 0.096 | 0.087 | 0.115 | 0.106 |
| Ratio 0° C./60° C. | 1.30 | 1.95 | 2.49 | 2.10 | 2.21 | 1.18 | 1.42 |

What is claimed is:

1. A blocked mercaptosilane selected from the group consisting of:

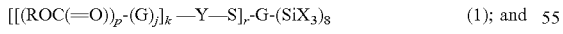  (1); and

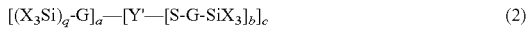  (2)

wherein

Y is a polyvalent species $(Q)_zA(=E)$ selected from the group consisting of —C(=NR)—; —SC(=NR)—; —SC(=O)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; —(—S)P(=O)—; —P(=O)(—)$_2$—; —(—S)P(=S)—; —P(=O)(—)$_2$; (—NR)$_2$P(=O)—; (—O)(—NR)P(=O)—; —(—O)P(=O)—; —(—NR)P(=O)—; (—NR)$_2$P(=S)—; (—NR)(—S)P(=S)—; (—O)(—NR)P(=S)—; —(—O)P(=S)—; and —(—NR)P(=S)—;

Y' is a polyvalent species $(O)_zA(=E)$ selected from the group consisting of —C(=NR)—; —SC(=NR)—; —SC(=O)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—;

wherein the atom A, attached to unsaturated heteroatom E is attached to the sulfur which in turn is linked via a group G to the silicon atom;

each R is chosen independently from hydrogen, straight, cyclic, or branched alkyl that may or may not contain carbon-carbon double bond, an alkenyl groups, an aryl groups, and/or aralkl groups, with each R contains from 1 to 18 carbon atoms;

each G is independently a monovalent or polyvalent group derived by substitution of alkyl, alkenyl, aryl, or aralkyl wherein G can contain from 1 to 18 carbon atom; wherein at least one G is polyvalent, and if G is monovalent, G can be a hydrogen atom;

X is independently selected from the group consisting of —Cl, —Br, RO—, RC(=O)O—, $R_2C$=NO—, $R_2NO$—, $R_2N$—, —R, and —$(OSiR_2)t(OSiR_3)$ wherein each R is as above and at least one X is not —R;

p is 0 to 5; r is 1 to 3; z is 0 to 2; q is 0 to 6; a is 0 to 7; b is 1 to 3; j is 0 to 1, but it may be 0 only if p is 1; c is 1 to 6; t is 0 to 5; s is 1 to 3; k is 1 to 2; with the provisos that (I) if A is carbon, sulfur, or sulfonyl, then (i) a+b is 2 and (ii) k is 1; (II) if A is phosphorous, then a+b is 3 unless both (i) c is greater than 1 and (ii) b is 1, in which case a is c+1; and (III) if A is phosphorous, then k is 2 and G is a monovalent or polyvalent group derived by substitution of alkyl, alkenyl, aryl, or aralkyl wherein G contains from 1 to 18 carbon atoms.

2. A blocked mercaptosilane according to claim 1 wherein a is selected from the group consisting of methyl, ethyl, propyl, isobutyl, phenyl, tolyl, phenethyl, norbornyl, norbornenyl, ethylnorbornyl, ethylnorbornenyl, ethylcyclohexyl, ethylcyclohexenyl, and cyclohexylcyclohexyl.

3. A blocked mercaptosilane according to claim 1 according to formula (1).

4. A blocked mercaptosilane according to claim 1 according to formula (2).

5. A blocked mercaptosilane according to claim 1 which has been partially hydrolyzed.

6. A blocked mercaptosilane according to claim 1 wherein Y is selected from the group consisting of: —SC(=O)—; —S(O)—; —OS(=O)—; —(S))=O)—; and —P(=P=O)(—)$_2$, and wherein Y' is selected from the group consisting of: —SC(=O)—; —S(=O)—; —OS(=O)—; and —P(=O)(—)$_2$.

7. The blocked mercaptosilane of claim 1 wherein Y is selected from the group consisting of —C(=NR)—and SC(=NR)—.

8. The blocked mercaptosilane of claim 1 wherein Y is selected from the group consisting of —S(=O)$_2$—; (—NR)S(=O)—; (—NR)S(=O)—; SS(=O)$_2$—.

9. A blocked mercaptosilane according to claim 1 wherein the sum of the carbon atoms within the G groups within the molecule is from 3 to 18.

10. A blocked mercaptosilane according to claim 1 wherein X is selected from the group consisting of methoxy, ethoxy, isobutoxy, propoxy, isopropoxy, acetoxy, and oximato.

11. A blocked mercaptosilane according to claim 1 wherein p is 0 to 2; X is RO— or RC(=O)O—; R is selected from the group consisting of hydrogen, phenyl, isopropyl, cyclohexyl, isobutyl; and G is a substituted phenyl or substituted straight chain alkyl of $C_2$ to $C_{12}$.

* * * * *